(12) United States Patent
Oikawa et al.

(10) Patent No.: US 11,219,650 B2
(45) Date of Patent: *Jan. 11, 2022

(54) AGENT FOR PREVENTING OR TREATING SMALL INTESTINAL INJURY INDUCED BY SPECIFIC NSAID AND PPI

(71) Applicant: Biofermin Pharmaceutical Co., Ltd., Kobe (JP)

(72) Inventors: Yosuke Oikawa, Kobe (JP); Yoshiki Tanaka, Kobe (JP); Hiroshi Ohno, Kobe (JP); Masaki Shimakawa, Kobe (JP)

(73) Assignee: Biofermin Pharmaceutical Co., Ltd., Kobe (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/759,683

(22) PCT Filed: Oct. 22, 2018

(86) PCT No.: PCT/JP2018/039157
§ 371 (c)(1),
(2) Date: Apr. 27, 2020

(87) PCT Pub. No.: WO2019/087841
PCT Pub. Date: May 9, 2019

(65) Prior Publication Data
US 2020/0338143 A1    Oct. 29, 2020

(51) Int. Cl.
| | | |
|---|---|---|
| *A61K 35/745* | (2015.01) |
| *A23L 33/135* | (2016.01) |
| *A61P 1/00* | (2006.01) |
| *A61K 8/99* | (2017.01) |
| *A61K 45/06* | (2006.01) |

(52) U.S. Cl.
CPC .......... *A61K 35/745* (2013.01); *A23L 33/135* (2016.08); *A61K 8/99* (2013.01); *A61P 1/00* (2018.01); *A61K 45/06* (2013.01)

(58) Field of Classification Search
None
See application file for complete search history.

(56) References Cited

FOREIGN PATENT DOCUMENTS

| | | |
|---|---|---|
| JP | 2000-507614 A | 6/2000 |
| JP | 2007-507485 A | 3/2007 |
| WO | WO 98/20870 A1 | 5/1998 |
| WO | WO 2005/032567 A2 | 4/2005 |

OTHER PUBLICATIONS

Amagase, Kikuko et al., "Effect of Probiotic Preparations on Loxoprofen-Induced Small Intestinal Lesions in Rats" Ulcer Research, 2013, pp. 25-29, vol. 40.
Fukuda, Shinji et al., "Bifidobacteria can protect from enteropathogenic infection through production of acetate" Nature, Jan. 2011, pp. 543-547, vol. 469.
Vulevic, J. et al., "In vitro effects of phosphatidylcholine and transgalactooligosaccharides on the production of 1,2-sn-diacylglycerol by Bifidobacterium longum biovar infantis" Journal of Applied Microbiology, 2008, pp. 1678-1685, vol. 105t.
Wallace, John L. et al., "Proton Pump Inhibitors Exacerbate NSAID-Induced Small Intestinal Injury by Inducing Dysbiosis" Gastroenterology, Oct. 2011, pp. 1314-1322.
International Preliminary Report on Patentability for PCT/JP2018/039157 dated May 5, 2020.

*Primary Examiner* — Brian Gangle
(74) *Attorney, Agent, or Firm* — Knobbe, Martens, Olson & Bear, LLP

(57) ABSTRACT

An object of the present invention is to provide an agent for preventing or treating small intestinal injury induced by an NSAID with a half-life of less than 14 hours and a proton pump inhibitor. The present invention provides an agent for preventing or treating small intestinal injury induced by a non-steroidal anti-inflammatory drug with a half-life of less than 14 hours and a proton pump inhibitor, and an agent for preventing or treating a fat-associated disease and/or inflammation accompanying the small intestinal injury, the agents comprising a *Bifidobacterium* bacterium or a processed product thereof.

5 Claims, 8 Drawing Sheets

AGENT FOR PREVENTING OR TREATING SMALL INTESTINAL INJURY INDUCED BY SPECIFIC NSAID AND PPI

CROSS REFERENCE TO RELATED APPLICATIONS

This application is a U.S. National Phase Application of PCT International Application Number PCT/JP2018/039157, filed on Oct. 22, 2018, designating the United States of America and published in the Japanese language, which is an International Application of and claims the benefit of priority to Japanese Patent Application No. 2017-211456, filed on Nov. 1, 2017. The disclosures of the above-referenced applications are hereby expressly incorporated by reference in their entireties.

TECHNICAL FIELD

The present invention relates to an agent for preventing or treating small intestinal injury induced by a specific non-steroidal anti-inflammatory drug (NSAID) and a proton pump inhibitor (PPI), and an agent for preventing or treating a fat-associated disease and/or inflammation accompanying the small intestinal injury. In particular, the present invention relates to an agent for preventing or treating small intestinal injury induced by a non-steroidal anti-inflammatory drug with a half-life of less than 14 hours and a proton pump inhibitor, and an agent for preventing or treating a fat-associated disease and/or inflammation accompanying the small intestinal injury.

BACKGROUND ART

Naproxen, which is a member of non-steroidal anti-inflammatory drugs (also called NSAIDs), in combination with omeprazole, which is a member of proton pump inhibitors (also called PPIs), is known to induce small intestinal injury (Non-Patent Literature 1).

However, a combination of the NSAID sulindac and the PPI omeprazole does not induce small intestinal injury, according to the findings by the present inventors (see Comparative Example 1 described later). That is, NSAIDs and PPIs do not always induce small intestinal injury.

CITATION LIST

Non-patent Literature

Non-Patent Literature 1: JOHN L. WALLACE et al., "Proton Pump Inhibitors Exacerbate NSAID-Induced Small Intestinal Injury by Inducing Dysbiosis", Gastroenterology, 2011; 141; 1314-1322.

SUMMARY OF INVENTION

Technical Problem

An object of the present invention is to provide an agent for preventing or treating small intestinal injury induced by an NSAID with a half-life of less than 14 hours and a proton pump inhibitor.

Solution to Problem

The present invention relates to the following.
(1) An agent for preventing or treating small intestinal injury induced by a non-steroidal anti-inflammatory drug with a half-life of less than 14 hours and a proton pump inhibitor, the agent comprising a *Bifidobacterium* bacterium or a processed product thereof.
(2) The agent according to the above (1), wherein the non-steroidal anti-inflammatory drug with a half-life of less than 14 hours is one or more selected from the group consisting of aspirin, loxoprofen, ibuprofen, diclofenac, acetaminophen, celecoxib, etodolac, pranoprofen, flurbiprofen axetil, lornoxicam, tiaramide, tramadol, zaltoprofen, and pharmaceutically acceptable salts thereof.
(3) The agent according to the above (1) or (2), wherein the proton pump inhibitor is one or more selected from the group consisting of omeprazole, lansoprazole, rabeprazole, esomeprazole, vonoprazan, tegoprazan, (R)-2-[4(2, 2-dimethyl-1,3-dioxan-5-yl)methoxy-3,5-dimethylpyridin-2-yl]methylsulfinyl-1H-benzimidazole, and pharmaceutically acceptable salts thereof.
(4) The agent according to any one of the above (1) to (3), wherein the processed product of the *Bifidobacterium* bacterium contains acetic acid.
(5) A pharmaceutical composition, a food composition or a cosmetic composition for preventing or treating small intestinal injury induced by a non-steroidal anti-inflammatory drug with a half-life of less than 14 hours and a proton pump inhibitor, the composition comprising the agent according to any one of the above (1) to (4).
(6) Use of a *Bifidobacterium* bacterium or a processed product thereof for production of the agent or the composition according to any one of the above (1) to (5).
(6-2) The use according to the above (6), wherein the non-steroidal anti-inflammatory drug with a half-life of less than 14 hours is one or more selected from the group consisting of aspirin, loxoprofen, ibuprofen, diclofenac, acetaminophen, celecoxib, etodolac, pranoprofen, flurbiprofen axetil, lornoxicam, tiaramide, tramadol, zaltoprofen, and pharmaceutically acceptable salts thereof.
(6-3) The use according to the above (6) or (6-2), wherein the proton pump inhibitor is one or more selected from the group consisting of omeprazole, lansoprazole, rabeprazole, esomeprazole, vonoprazan, tegoprazan, (R)-2-[4(2, 2-dimethyl-1,3-dioxan-5-yl)methoxy-3,5-dimethylpyridin-2-yl]methylsulfinyl-1H-benzimidazole, and pharmaceutically acceptable salts thereof.
(6-4) The use according to any one of the above (6) to (6-3), wherein the processed product of the *Bifidobacterium* bacterium contains acetic acid.
(6-5) The use according to any one of the above (6) to (6-4), wherein the *Bifidobacterium* bacterium or a processed product thereof is contained in a pharmaceutical composition, a food composition, or a cosmetic composition.
(7) An agent for preventing or treating a fat-associated disease and/or inflammation accompanying small intestinal injury induced by a non-steroidal anti-inflammatory drug with a half-life of less than 14 hours and a proton pump inhibitor, the agent comprising a *Bifidobacterium* bacterium or a processed product thereof.
(7-2) The agent according to the above (7), wherein the non-steroidal anti-inflammatory drug with a half-life of less than 14 hours is one or more selected from the group consisting of aspirin, loxoprofen, ibuprofen, diclofenac, acetaminophen, celecoxib, etodolac, pranoprofen, flurbiprofen axetil, lornoxicam, tiaramide, tramadol, zaltoprofen, and pharmaceutically acceptable salts thereof.
(7-3) The agent according to the above (7) or (7-2), wherein the proton pump inhibitor is one or more selected from the group consisting of omeprazole, lansoprazole, rabeprazole, esomeprazole, vonoprazan, tegoprazan, (R)-2-[4(2,2-dimethyl-1,3-dioxan-5-yl)methoxy-3,5-dimethylpyridin-2-yl]methylsulfinyl-1H-benzimidazole, and pharmaceutically acceptable salts thereof.

(7-4) The agent according to any one of the above (7) to (7-3), wherein the processed product of the *Bifidobacterium* bacterium contains acetic acid.

(7-5) A pharmaceutical composition, a food composition or a cosmetic composition for preventing or treating small intestinal injury induced by a non-steroidal anti-inflammatory drug with a half-life of less than 14 hours and a proton pump inhibitor, the composition comprising the agent according to any one of the above (7) to (7-4).

(8) A method for preventing or treating small intestinal injury induced by a non-steroidal anti-inflammatory drug with a half-life of less than 14 hours and a proton pump inhibitor, the method comprising the step of administering a *Bifidobacterium* bacterium or a processed product thereof to a human or a non-human animal.

(8-2) The method according to the above (8), wherein the non-steroidal anti-inflammatory drug with a half-life of less than 14 hours is one or more selected from the group consisting of aspirin, loxoprofen, ibuprofen, diclofenac, acetaminophen, celecoxib, etodolac, pranoprofen, flurbiprofen axetil, lornoxicam, tiaramide, tramadol, zaltoprofen, and pharmaceutically acceptable salts thereof.

(8-3) The method according to the above (8) or (8-2), wherein the proton pump inhibitor is one or more selected from the group consisting of omeprazole, lansoprazole, rabeprazole, esomeprazole, vonoprazan, tegoprazan, (R)-2-[4(2,2-dimethyl-1,3-dioxan-5-yl)methoxy-3,5-dimethylpyridin-2-yl]methylsulfinyl-1H-benzimidazole, and pharmaceutically acceptable salts thereof.

(8-4) The method according to any one of the above (8) to (8-3), wherein the processed product of the *Bifidobacterium* bacterium contains acetic acid.

(8-5) The method according to any one of the above (8) to (8-4), wherein the *Bifidobacterium* bacterium or a processed product thereof is contained in a pharmaceutical composition, a food composition, or a cosmetic composition.

(9) A *Bifidobacterium* bacterium or a processed product thereof for use in prevention or treatment of small intestinal injury induced by a non-steroidal anti-inflammatory drug with a half-life of less than 14 hours and a proton pump inhibitor.

(9-2) The *Bifidobacterium* bacterium or a processed product thereof for use according to the above (9), wherein the non-steroidal anti-inflammatory drug with a half-life of less than 14 hours is one or more selected from the group consisting of aspirin, loxoprofen, ibuprofen, diclofenac, acetaminophen, celecoxib, etodolac, pranoprofen, flurbiprofen axetil, lornoxicam, tiaramide, tramadol, zaltoprofen, and pharmaceutically acceptable salts thereof.

(9-3) The *Bifidobacterium* bacterium or a processed product thereof for use according to the above (9) or (9-2), wherein the proton pump inhibitor is one or more selected from the group consisting of omeprazole, lansoprazole, rabeprazole, esomeprazole, vonoprazan, tegoprazan, (R)-2-[4(2,2-dimethyl-1,3-dioxan-5-yl)methoxy-3,5-dimethylpyridin-2-yl]methylsulfinyl-1H-benzimidazole, and pharmaceutically acceptable salts thereof.

(9-4) The *Bifidobacterium* bacterium or a processed product thereof for use according to any one of the above (9) to (9-3), wherein the processed product of the *Bifidobacterium* bacterium contains acetic acid.

(9-5) The *Bifidobacterium* bacterium or a processed product thereof for use according to any one of the above (9) to (9-4), wherein the *Bifidobacterium* bacterium or a processed product thereof is contained in a pharmaceutical composition, a food composition, or a cosmetic composition.

(10) Use of a *Bifidobacterium* bacterium or a processed product thereof for prevention or treatment of small intestinal injury induced by a non-steroidal anti-inflammatory drug with a half-life of less than 14 hours and a proton pump inhibitor.

(10-2) The use according to the above (10), wherein the non-steroidal anti-inflammatory drug with a half-life of less than 14 hours is one or more selected from the group consisting of aspirin, loxoprofen, ibuprofen, diclofenac, acetaminophen, celecoxib, etodolac, pranoprofen, flurbiprofen axetil, lornoxicam, tiaramide, tramadol, zaltoprofen, and pharmaceutically acceptable salts thereof.

(10-3) The use according to the above (10) or (10-2), wherein the proton pump inhibitor is one or more selected from the group consisting of omeprazole, lansoprazole, rabeprazole, esomeprazole, vonoprazan, tegoprazan, (R)-2-[4(2,2-dimethyl-1,3-dioxan-5-yl)methoxy-3,5-dimethylpyridin-2-yl]methylsulfinyl-1H-benzimidazole, and pharmaceutically acceptable salts thereof.

(10-4) The use according to any one of the above (10) to (10-3), wherein the processed product of the *Bifidobacterium* bacterium contains acetic acid.

(10-5) The use according to any one of the above (10) to (10-4), wherein the *Bifidobacterium* bacterium or a processed product thereof is contained in a pharmaceutical composition, a food composition, or a cosmetic composition.

(11) A method for preventing or treating a fat-associated disease and/or inflammation accompanying small intestinal injury induced by a non-steroidal anti-inflammatory drug with a half-life of less than 14 hours and a proton pump inhibitor, the method comprising the step of administering a *Bifidobacterium* bacterium or a processed product thereof to a human or a non-human animal.

(11-2) The method according to the above (11), wherein the non-steroidal anti-inflammatory drug with a half-life of less than 14 hours is one or more selected from the group consisting of aspirin, loxoprofen, ibuprofen, diclofenac, acetaminophen, celecoxib, etodolac, pranoprofen, flurbiprofen axetil, lornoxicam, tiaramide, tramadol, zaltoprofen, and pharmaceutically acceptable salts thereof.

(11-3) The method according to the above (11) or (11-2), wherein the proton pump inhibitor is one or more selected from the group consisting of omeprazole, lansoprazole, rabeprazole, esomeprazole, vonoprazan, tegoprazan, (R)-2-[4(2,2-dimethyl-1,3-dioxan-5-yl)methoxy-3,5-dimethylpyridin-2-yl]methylsulfinyl-1H-benzimidazole, and pharmaceutically acceptable salts thereof.

(11-4) The method according to any one of the above (11) to (11-3), wherein the processed product of the *Bifidobacterium* bacterium contains acetic acid.

(11-5) The method according to any one of the above (11) to (11-4), wherein the *Bifidobacterium* bacterium or a processed product thereof is contained in a pharmaceutical composition, a food composition, or a cosmetic composition.

(12) A *Bifidobacterium* bacterium or a processed product thereof for use in prevention or treatment of a fat-associated disease and/or inflammation accompanying small intestinal injury induced by a non-steroidal anti-inflammatory drug with a half-life of less than 14 hours and a proton pump inhibitor.

(12-2) The *Bifidobacterium* bacterium or a processed product thereof for use according to the above (12), wherein the non-steroidal anti-inflammatory drug with a half-life of less than 14 hours is one or more selected from the group consisting of aspirin, loxoprofen, ibuprofen, diclofenac, acetaminophen, celecoxib, etodolac, pranoprofen, flurbiprofen axetil, lornoxicam, tiaramide, tramadol, zaltoprofen, and pharmaceutically acceptable salts thereof.

(12-3) The *Bifidobacterium* bacterium or a processed product thereof for use according to the above (12) or (12-2), wherein the proton pump inhibitor is one or more selected from the group consisting of omeprazole, lansoprazole, rabeprazole, esomeprazole, vonoprazan, tegoprazan, (R)-2-[4(2,2-dimethyl-1,3-dioxan-5-yl)methoxy-3,5-dimethylpyridin-2-yl]methylsulfinyl-1H-benzimidazole, and pharmaceutically acceptable salts thereof.

(12-4) The *Bifidobacterium* bacterium or a processed product thereof for use according to any one of the above (12) to (12-3), wherein the processed product of the *Bifidobacterium* bacterium contains acetic acid.

(12-5) The *Bifidobacterium* bacterium or a processed product thereof for use according to any one of the above (12) to (12-4), wherein the *Bifidobacterium* bacterium or a processed product thereof is contained in a pharmaceutical composition, a food composition, or a cosmetic composition.

(13) Use of a *Bifidobacterium* bacterium or a processed product thereof for prevention or treatment of a fat-associated disease and/or inflammation accompanying small intestinal injury induced by a non-steroidal anti-inflammatory drug with a half-life of less than 14 hours and a proton pump inhibitor.

(13-2) The use according to the above (13), wherein the non-steroidal anti-inflammatory drug with a half-life of less than 14 hours is one or more selected from the group consisting of aspirin, loxoprofen, ibuprofen, diclofenac, acetaminophen, celecoxib, etodolac, pranoprofen, flurbiprofen axetil, lornoxicam, tiaramide, tramadol, zaltoprofen, and pharmaceutically acceptable salts thereof.

(13-3) The use according to the above (13) or (13-2), wherein the proton pump inhibitor is one or more selected from the group consisting of omeprazole, lansoprazole, rabeprazole, esomeprazole, vonoprazan, tegoprazan, (R)-2-[4(2,2-dimethyl-1,3-dioxan-5-yl)methoxy-3,5-dimethylpyridin-2-yl]methylsulfinyl-1H-benzimidazole, and pharmaceutically acceptable salts thereof.

(13-4) The use according to any one of the above (13) to (13-3), wherein the processed product of the *Bifidobacterium* bacterium contains acetic acid.

(13-5) The use according to any one of the above (13) to (13-4), wherein the *Bifidobacterium* bacterium or a processed product thereof is contained in a pharmaceutical composition, a food composition, or a cosmetic composition.

Advantageous Effects of Invention

The present invention provides an agent for preventing or treating small intestinal injury induced by an NSAID with a half-life of less than 14 hours and a PPI.

The present invention also provides an agent for preventing or treating a fat-associated disease and/or inflammation accompanying small intestinal injury induced by an NSAID with a half-life of less than 14 hours and a PPI.

DESCRIPTION OF EMBODIMENTS

Figure 1:
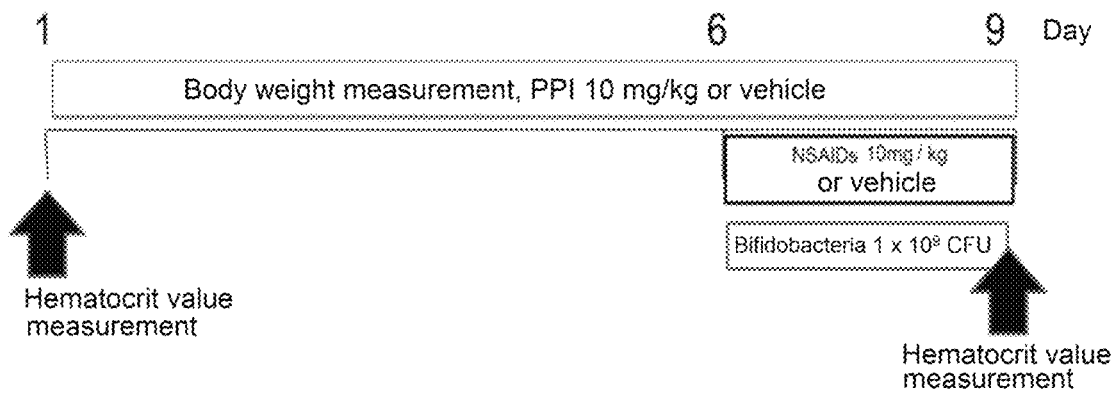
FIG. 1 shows the experimental schedule for Test 1.
Figure 2:
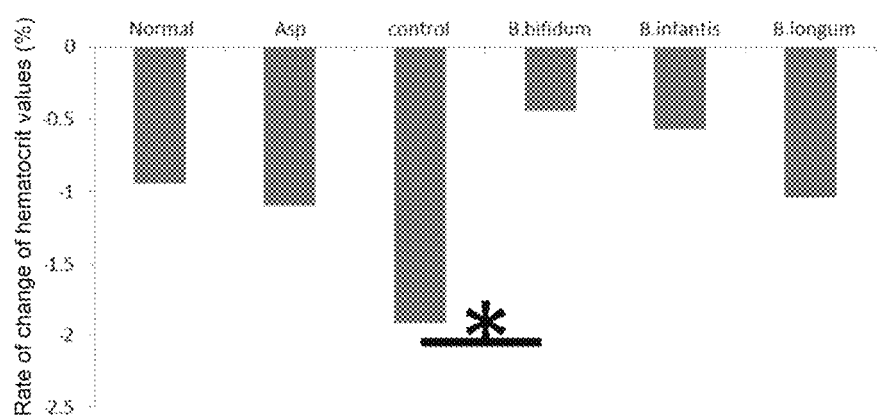
FIG. 2 shows the results of experiments for evaluating inhibitory effects on small intestinal injury induced by aspirin and omeprazole, as assessed by determining the rate of change of hematocrit values (%). The data show the mean (n=5). *; $p<0.05$ by the Dunnett test.

The present invention provides an agent for preventing or treating small intestinal injury induced by a non-steroidal anti-inflammatory drug with a half-life of less than 14 hours and a proton pump inhibitor, the agent comprising a *Bifidobacterium* bacterium or a processed product thereof. The agent of the present invention is only required to contain the bacterium or a processed product thereof, and the agent may further contain another ingredient.

*Bifidobacterium* Bacteria

*Bifidobacterium* bacteria include, for example, *Bifidobacterium bifidum*, *Bifidobacterium longum* (*B. longum*), *Bifidobacterium breve* (*B. breve*), *Bifidobacterium adolescentis* (*B. adolescentis*), *Bifidobacterium infantis* (*B. infantis*), *Bifidobacterium pseudolongum* (*B. pseudolongum*), *Bifidobacterium thermophilum* (*B. thermophilum*), etc. A particularly preferred strain of *Bifidobacterium bifidum* is the *Bifidobacterium bifidum* G9-1 strain. The *Bifidobacterium* bacteria may be those other than *Bifidobacterium adolescentis* (*B. adolescentis*) and/or *Bifidobacterium dentium* (*B. dentium*). The *Bifidobacterium* bacteria used in the present invention may be bacteria that are identified by comparison with known *Bifidobacterium* bacteria in terms of the characteristics, including, for example, morphological characteristics (for example, the shape of colonies, the shape of cells, etc.), physiological or biochemical characteristics (for example, utilization of sugars, growth temperature, an optimal pH, etc.), and chemotaxonomic characteristics (the fatty acid composition of bacterial cells, etc.); or may be bacteria that are identified based on nucleotide sequence analysis of 16S rRNA genes. The *Bifidobacterium* bacteria used may be a single strain or a mixture of two or more strains.

These bacteria are easily available from, for example, organizations such as ATCC or IFO; the Japan Bifidus Foundation; and Incorporated Administrative Agency National Institute of Technology and Evaluation, Patent Microorganisms Depositary; etc. A commercially available bacteria may also be used as appropriate.

For example, *Bifidobacterium bifidum* G9-1 was internationally deposited on Sep. 30, 2009 (Date of the original deposit: Sep. 17, 2009) under Accession No. NITE BP-817 in Incorporated Administrative Agency National Institute of Technology and Evaluation, Patent Microorganisms Depositary (NPMD) (address: #122, 2-5-8 Kazusakamatari, Kisarazu-shi, Chiba 292-0818 Japan).

Bacteria or Processed Products Thereof

The *Bifidobacterium* bacteria of the present invention may be viable bacteria and/or dead bacteria, or may be a processed product of the bacteria. The processed product of the bacteria refers to a product produced by subjecting the *Bifidobacterium* bacteria to certain processing, and the processing is not limited to a particular one. Specific examples of the processed product include a suspension of the bacterial cells disrupted by, e.g., sonication; culture medium or culture supernatant of the bacterial cells; solid residues separated from such disrupted cell suspension, culture medium or culture supernatant by a solid-liquid separation technique, such as filtration or centrifugation; etc. The processed product also includes a processed solution produced by removing the cell walls by an enzymatic or mechanical technique; intracellular components of the bacteria, such as protein complexes (proteins, lipoproteins, glycoproteins, etc.) or peptide complexes (peptides, glycopeptides, etc.), obtained by trichloroacetic acid treatment or salting-out process; extracellular components of the bacteria secreted by the bacteria to the outside of the cell membrane; etc. The processed product further includes concentrates, diluted products, or dried products of the above processed products. The processed product in the present invention also includes a further processed product prepared by subjecting a disrupted (e.g., sonicated) bacterial cell suspension, bacterial cell culture medium or culture supernatant, or the like to, for example, separation by various types of chromatography, etc. The processed product in the present invention further includes dead cells of the *Bifidobacterium* bacteria of the present invention. The dead bacterial cells can be prepared by, for example, enzymatic treatment, heat-treatment at about 100° C., drug treatment such as antibiotics, chemical treatment such as formalin, radiation treatment such as γ-rays, etc. The processed product in the present invention also includes acetic acid. Acetic acid is obtained, for example, as a metabolite of viable cells of *Bifidobacterium* bacteria, and may be contained in the culture medium or culture supernatant of *Bifidobacterium* bacteria.

The bacteria used in the present invention may be a dried product (dried bacterial cells), and are preferably single micron-sized dried bacterial cells. The term "dried bacterial cells" typically refers to individual dried bacterial cells or a gathered mass of dried bacterial cells. The term "single micron-sized" refers to a size of 1 to 10 μm when rounded to the nearest whole number. When the *Bifidobacterium* bacteria used in the present invention are in the form of single micron-sized dried bacterial cells, the proportion of viable bacteria in a bacterial formulation is high, and therefore the formulation exhibits a high preventive or therapeutic effect on small intestinal injury induced by an NSAID with a half-life of less than 14 hours and a PPI.

A preferred production method of the dried bacterial cells will be described below. Bacterial cells as described above are dispersed in a solvent to prepare a bacterial cell liquid. The solvent may be a known solvent in the art, but is preferably water. If desired, ethanol may be added. When the bacteria in a solvent containing ethanol are subjected to drying, ethanol evaporates first and water then evaporates, which enables step-wise drying. The bacterial cell liquid may be in the form of a suspension. The solvent of the suspension may be the same as described above. When the bacteria are suspended in a solvent, a suspending agent such as sodium alginate may be used.

An additive conventionally used in the art, including, for example, a protective agent, an excipient, a binder, a disintegrant and an antistatic, may be added to the bacterial cell liquid in a usual amount.

The bacterial cell liquid may be subjected to drying with a spray dryer to prepare dried bacterial cells. The spray dryer is preferably equipped with an atomization device capable of forming single micron-sized spray droplets. Spray droplets with a very small particle size will have a large surface area per unit mass, and therefore the spray droplets efficiently contact with warm drying air and in turn the productivity improves.

The term "single micron-sized liquid droplets" refers to spray droplets having a particle size of 1 to 10 μm when rounded to the nearest whole number.

Examples of the spray dryer include a spray dryer equipped with an atomization device that may be, for example, a rotary atomizer (a rotary disk), a pressure nozzle, or a two-fluid or four-fluid nozzle utilizing the force of compressed gas.

The spray dryer is preferably one of the above described types capable of forming single micron-sized spray droplets, but preferred is a spray dryer equipped with a four-fluid nozzle.

In such a spray dryer equipped with a four-fluid nozzle, the four-fluid nozzle may have a structure in which a gas passage is combined with a liquid passage to form a single unit, and two sets of the unit are symmetrically disposed at the edge of the nozzle, thereby providing the nozzle edge with slopes for directing the flow of a fluid.

The spray dryer is preferably equipped with an external mixing atomization device capable of directing compressed gas and liquid from both sides to collide at a single focal point at the tip of the nozzle edge. This type of atomization device is advantageous in that nozzle clogging is prevented and spraying can be performed for a long period of time.

Examples of the compressed gas include inert gas, such as air, carbon dioxide gas, nitrogen gas, argon gas, etc. Especially when easily oxidized materials or the like are spray-dried, inert gas such as carbon dioxide gas, nitrogen gas, argon gas, etc. is preferred.

The pressure of the compressed gas is usually about 1 to 15 kgf/cm², preferably about 3 to 8 kgf/cm².

The gas flow rate at the nozzle is usually about 1 to 100 L/min, preferably about 10 to 20 L/min, per mm of the nozzle edge.

Typically, after spraying, the spray droplets are allowed to contact with warm drying air in a drying chamber to evaporate the moisture to give dried bacterial cells.

The inlet temperature of the drying chamber is usually about 2 to 400° C., preferably about 5 to 250° C., and more preferably about 5 to 150° C. Even when the inlet temperature is as high as about 200 to 400° C., the temperature in the drying chamber does not become excessively high due to heat of evaporation of moisture. The death of or damage to living bacteria can be prevented to some extent by reducing the retention time in the drying chamber.

The outlet temperature is usually about 0 to 120° C., preferably about 5 to 90° C., and more preferably about 5 to 70° C.

Reduction in the particle size of the dried bacterial cells as described above increases the proportion of viable bacteria in a bacterial formulation, which advantageously provides a formulation with a high proportion of viable bacteria.

In other words, the bacterial cell liquid is preferably sprayed into single micron-sized spray droplets to produce single micron-sized dried bacterial cells. Spray droplets with a small particle size will have a large surface area per unit mass, and therefore the spray droplets efficiently contact with warm drying air, and in turn the death of or damage to bacterial cells due to the heat from warm drying air is prevented to the best extent possible. As a result, the proportion of viable bacteria is increased, and dried bacterial cells contain a large number of viable bacteria.

Non-Steroidal Anti-Inflammatory Drugs (NSAIDs) with Half-Life of Less Than 14 Hours The NSAIDs according to the present invention may be, for example, acetylsalicylic acid (aspirin), loxoprofen, ibuprofen, diclofenac, acetaminophen, celecoxib, etodolac, lornoxicam, tiaramide, tramadol, zaltoprofen, pranoprofen, or flurbiprofen axetil or a pharmaceutically acceptable salt thereof. The NSAIDs according to the present invention may be a single type or a combination of two or more types.

The pharmaceutically acceptable salt may include, for example, a salt with an inorganic base, a salt with an organic base, a salt with an inorganic acid, a salt with an organic acid, a salt with a basic amino acid, a salt with an acidic amino acid, and the like.

Examples of suitable salts with an inorganic base include for example, alkali metal salts, such as sodium salts and potassium salts; alkaline earth metal salts, such as calcium salts and magnesium salts; aluminum salts; ammonium salts; and the like.

Examples of suitable salts with an organic base include, for example, salts with trimethylamine, triethylamine, pyridine, picoline, ethanolamine, diethanolamine, triethanolamine, dicyclohexylamine, N,N'-dibenzylethylenediamine, or the like.

Examples of suitable salts with an inorganic acid include, for example, salts with hydrochloric acid, hydrobromic acid, nitric acid, sulfuric acid, phosphoric acid, or the like.

Examples of suitable salts with an organic acid include, for example, salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, or the like.

Examples of suitable salts with a basic amino acid include, for example, salts with arginine, lysine, ornithine, or the like. Examples of suitable salts with an acidic amino acid include, for example, salts with aspartic acid, glutamic acid, or the like.

Especially preferred are salts with an inorganic base, and preferred are sodium salts (for example, diclofenac sodium) and potassium salts.

Proton Pump Inhibitors (PPIs)

The PPIs according to the present invention may be, for example, omeprazole, lansoprazole, rabeprazole, esomeprazole, vonoprazan, tegoprazan, or (R)-2-[4(2,2-dimethyl-1,3-dioxan-5-yl)methoxy-3,5-dimethylpyridin-2-yl]methyl-sulfinyl-1H-benzimidazole, or a pharmaceutically acceptable salt thereof. The PPIs according to the present invention may be a single type or a combination of two or more types.

The PPIs according to the present invention can be produced by ordinary chemical reactions, or can be purchased as commercially available products.

The pharmaceutically acceptable salt may include, for example, a salt with an inorganic base, a salt with an organic base, a salt with an inorganic acid, a salt with an organic acid, a salt with a basic amino acid, a salt with an acidic amino acid, and the like.

Examples of suitable salts with an inorganic base include for example, alkali metal salts, such as sodium salts and potassium salts; alkaline earth metal salts, such as calcium salts and magnesium salts; aluminum salts; ammonium salts; and the like.

Examples of suitable salts with an organic base include, for example, salts with trimethylamine, triethylamine, pyridine, picoline, ethanolamine, diethanolamine, triethanolamine, dicyclohexylamine, N,N'-dibenzylethylenediamine, or the like.

Examples of suitable salts with an inorganic acid include, for example, salts with hydrochloric acid, hydrobromic acid, nitric acid, sulfuric acid, phosphoric acid, or the like.

Examples of suitable salts with an organic acid include, for example, salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, or the like.

Examples of suitable salts with a basic amino acid include, for example, salts with arginine, lysine, ornithine, or the like. Examples of suitable salts with an acidic amino acid include, for example, salts with aspartic acid, glutamic acid, or the like.

Especially preferred are salts with an inorganic base, and preferred are sodium salts (for example, rabeprazole sodium) and potassium salts.

Small Intestinal Injury

Small intestinal injury according to the present invention may be any abnormality in the small intestine that is induced by administration of an NSAID with a half-life of less than 14 hours and a PPI. Specific examples of small intestinal injury include ulcers and accompanying conditions, such as small intestinal bleeding, decreased blood hematocrit values, enhanced intestinal permeability, and a decreased number of small intestinal villi.

The small intestine may be the jejunum and/or ileum.

Prevention or Treatment

The term "prevention" as used herein includes inhibition or delay of development of symptoms or diseases. The term "treatment" as used herein includes complete healing of symptoms or diseases, and alleviation of symptoms.

Prevention or Treatment of Small Intestinal Injury

Whether the agent of the present invention has a preventive or therapeutic effect on small intestinal injury can be determined by, for example, the methods as described later in Examples.

Specifically, the preventive or therapeutic effect of the agent of the present invention on small intestinal injury can be confirmed by, for example, evaluating whether a blood hematocrit value after administration of an NSAID, a PPI and the agent of the present invention is higher than that after administration of the NSAID and the PPI. When the blood hematocrit value after administration of an NSAID, a PPI and the agent of the present invention is "higher" than that after administration of the NSAID and the PPI, the agent of the present invention is determined to have a preventive or therapeutic effect on small intestinal injury. Preferably there is a significant difference between these hematocrit values, but there may be a tendency to significance. The hematocrit values can be measured by a known method or a method known per se, for example, by the Wintrobe method using Wintrobe tubes, the high speed centrifugation method (microhematocrit method) using capillary tubes, or other methods.

Whether the agent of the present invention has a preventive or therapeutic effect on small intestinal injury can be determined by, for example, evaluating whether the agent has a preventive or therapeutic effect on enhanced intestinal permeability. When the level of intestinal permeability after administration of an NSAID, a PPI and the agent of the present invention is "lower" than that after administration of the NSAID and the PPI, the agent of the present invention is determined to have a preventive or therapeutic effect on small intestinal injury. Preferably there is a significant difference between these levels of intestinal permeability, but there may be a tendency to significance. The intestinal permeability can be measured by a known method or a method known per se, for example, by a method involving oral administration of a fluorescent dye, such as FITC, followed by measurement of the fluorescence intensity in the plasma, or other methods.

Whether the agent of the present invention has a preventive or therapeutic effect on small intestinal injury can be determined by, for example, evaluating whether the agent has a preventive or therapeutic effect on decrease in the number of villi in the small intestine. When the number of the villi in the small intestine after administration of an NSAID, a PPI and the agent of the present invention is "higher" than that after administration of the NSAID and the PPI, the agent of the present invention is determined to have a preventive or therapeutic effect on small intestinal injury. Preferably there is a significant difference between these numbers of the villi, but there may be a tendency to significance. The number of the villi can be measured by a known method or a method known per se, for example, by a method involving microscopic observations of histological sections of the small intestine, or other methods.

Prevention or Treatment of Fat-associated Diseases and/or Inflammation Accompanying Small Intestinal Injury Enhanced intestinal permeability and increased blood levels of endotoxin are also involved in the pathological mechanism of nonalcoholic fatty liver disease (NAFLD). Indeed, as previously reported, NAFLD patients have a significantly elevated level of blood endotoxin and significantly enhanced intestinal permeability (see, for example, the Journal of the Japanese Society of Internal Medicine, vol. 104, No. 1, 48-56, 2015, "NASH/NAFLD and Gut Microbiota," page 50, left column, lines 1 to 6 from the bottom). The pathological conditions of NAFLD include, for example, fatty change of the liver, liver cell damage, inflammation, fibrosis, and hepatocellular carcinoma (see, for example, the Journal of the Japanese Society of Internal Medicine, vol. 104, No. 1, 48-56, 2015, "NASH/NAFLD and Gut Microbiota," FIGS. 3 and 4).

Therefore, the agent of the present invention can be used to prevent or treat a fat-associated disease and/or inflammation accompanying small intestinal injury, as exemplified by NAFLD.

The fat-associated disease in the present invention is preferably a fat-associated disease caused by enhanced intestinal permeability. The agent of the present invention exhibits an excellent preventive or therapeutic effect on such a fat-associated disease. The fat-associated disease may be, for example, a fat-related disease or a disease that is developed in association with a fat-related disease. The fat-related disease may be, for example, a disease that is developed or aggravated by fat accumulation. Examples of the disease that is developed or aggravated by fat accumulation include metabolic syndrome, NAFLD (including nonalcoholic steatohepatitis (NASH)), hyperlipemia, etc. Metabolic syndrome is a condition that includes a cluster of diseases and abnormalities, and examples of the diseases and abnormalities include obesity (for example, lipid metabolic abnormalities, fatty liver, etc.), carbohydrate metabolic abnormalities, abnormal insulin resistance, heart diseases such as angina pectoris and myocardial infarction, arteriosclerotic diseases (for example, cerebral infarction, arteriosclerosis obliterans, etc.), etc. Examples of the disease that is developed in association with a fat-related disease include cirrhosis, liver cancer, etc.

The inflammation in the present invention is preferably inflammation caused by elevated levels of blood endotoxin due to enhanced intestinal permeability. The agent of the present invention exhibits an excellent preventive or therapeutic effect on such inflammation. The inflammation may be, for example, spontaneous inflammation, lasting inflammation, etc. The site of the inflammation may be the whole body or part of the body etc. The cause of the inflammation may be, for example, an external cause or an internal cause. Examples of the external cause include physical factors (for example, mechanical stimulus, heat, ultraviolet rays, etc.), chemical factors (for example, strong acids, strong alkalis, harmful chemicals, etc.), biological factors (for example, bacteria, viruses, parasites, etc.), etc. Examples of the internal cause include allergies, autoimmune disorders (for example, atopic dermatitis, rheumatoid arthritis, etc.), production of inflammatory substances (for example, endotoxin), functional disorders of organs, stress (for example, tendovaginitis, osteoarthritis), etc. The degree of the inflammation may range, for example, from mild to severe.

The preventive or therapeutic effect of the agent of the present invention on a fat-associated disease and/or inflammation can be confirmed by a known method or a method known per se. In an example, when the body weight measurement or the analysis of the amount of liver fat, the fat around the epididymis or other body fat by CT scan etc. indicates reduction in the body weight or the amount of the fat, the agent is determined to have a preventive or improving effect on obesity. In another example, when the pathological analysis of part of liver tissue for examination of lipid droplets and/or fibrosis indicates reduced lipid droplets and/or fibrosis, the agent is determined to have a preventive or therapeutic effect on fatty liver and/or liver fibrosis. In another example, when the analysis of expression of a gene involved in fibrosis of hepatocytes by quantitative real-time PCR etc. indicates reduced gene expression, the agent is determined to have a preventive or therapeutic effect on liver fibrosis. The quantitative real-time PCR can be performed using, for example, a fluorescent-labeled TaqMan probe or molecular beacon, etc. A TaqMan probe and a molecular beacon are oligonucleotide probes that have a homology with an internal sequence in the region to be amplified by PCR and is labeled with a fluorescent dye and a quencher. A TaqMan probe and a molecular beacon can be used in PCR reaction. In another example, when the measurement of the plasma levels of total cholesterol, ALT and AST indicates reduced levels of them, the agent is determined to have a maintaining or improving effect on liver function. In another example, when HOMA-IR calculated from the plasma levels of glucose and insulin by the formula (1) below indicates a reduced HOMA-IR value, the agent is determined to have an improving effect on glucose tolerance.

$$\text{HOMA-IR} = \text{Fasting plasma insulin}(\mu\text{IU/mL}) \times \text{Fasting plasma glucose}(\text{mg/dL})/405 \quad (1)$$

In another example, when the measurement of the plasma levels of endotoxin indicates reduced blood levels of endotoxin, the agent is determined to have a preventive or therapeutic effect on inflammation. In another example, when the analysis of the gene expression of proinflammatory cytokines etc. found in the plasma indicates reduced gene expression of the proinflammatory cytokines etc., the agent is determined to have a preventive or therapeutic effect on inflammation.

Agent

The agent of the present invention is only required to contain a *Bifidobacterium* bacterium or a processed product thereof, and may further contain as appropriate another ingredient depending on the dosage form, the mode of administration, the desired efficacy, etc. Examples of said another ingredient include another pharmacologically active ingredient, a carrier, an additive (for example, an antiseptic, a surfactant, a stabilizer, an isotonic agent, a pH adjuster, etc.), other bacteria than *Bifidobacterium* bacteria, etc. These ingredients may be used alone or in combination of two or more types. For the purpose of preventing or treating small intestinal injury induced by aspirin and omeprazole, the present invention may exclude the case where the agent comprises *Bifidobacterium adolescentis* and/or *Bifidobacterium dentium* as the *Bifidobacterium* bacteria.

Administration Method, Dosage Form, Etc. of the Agent

The mode of administration (or the dosage form) of the agent of the present invention may be any mode of administration (or any dosage form) that allows the agent to prevent or treat small intestinal injury induced by an NSAID with a half-life of less than 14 hours and a PPI. The agent may be administered, for example, via an oral route (as an oral agent) or a parenteral route (as a parenteral agent), etc.

The oral agent may be prepared by, for example, combining the agent of the present invention with a pharmaceutically acceptable carrier. Examples of the oral agent include, for example, solid dosage forms, such as tablets (for example, sugar-coated tablets etc.), pills, capsules, powders, coated tablets, granules, and troches; liquid dosage forms, such as solutions, suspensions, emulsions, syrups and elixirs; semi-solid dosage forms, such as jelly formulations; etc. Examples of the parenteral agent include, for example, injections (for example, subcutaneous, intravenous, intramuscular, and intraperitoneal injections, intravenous drips, etc.), suppositories (for example, rectal suppositories, vaginal suppositories, etc.), topical agents (for example, transdermal formulations, ointments, transnasal formulations, etc.), etc.

The dosage form of the agent of the present invention is not limited to a particular one, and may be, for example, a liquid, a fluid, a gel, a semi-solid, a solid, etc. The dosage form also includes liquid, fluid, gel, semi-solid, solid and other dosage forms that are prepared at the time of use.

Dosage of the Agent

The amount of the bacteria or a processed product thereof contained in the agent of the present invention is not limited to a particular one, but the amount calculated based on the dry mass of the bacteria may be, for example, about 0.0001% by mass to about 50% by mass, about 0.001% by mass to about 30% by mass, about 0.01% by mass to about 10% by mass, or the like relative to the total mass of the agent, and the amount calculated based on the dry mass of a processed product of the bacteria may be, for example, about 0.0001% by mass to about 50% by mass, about 0.001% by mass to about 30% by mass, about 0.01% by mass to about 10% by mass, or the like relative to the total mass of the agent.

The dosage of the agent of the present invention may be selected as appropriate depending on the dosage form, the route of administration, the subject of administration, the age and body weight of the subject, the intervals of administration, etc. The dosage of the agent when administered via an oral route may depend on the subject of administration (for example, an adult human), the intervals of administration (for example, one dose a day), etc., but the oral dose of the agent calculated based on the dry mass of the bacteria of the present invention may be, for example, about 0.0001 mg to about 100 g, about 0.001 mg to about 50 g, about 0.01 mg to about 20 g, about 0.1 mg to about 5 g, or the like, or the oral dose of the agent calculated based on the dry mass of a processed product of the bacteria of the present invention may be, for example, about 0.0001 mg to about 100 g, about 0.001 mg to about 50 g, about 0.01 mg to about 20 g, about 0.1 mg to about 5 g, or the like. When the agent of the present invention contains viable bacteria, the dosage of the agent calculated based on the number of viable bacteria is, for example, typically about 1 to $10^{12}$ cells/dose per adult human, preferably $10^1$ to $10^{11}$ cells/dose per adult human, and more preferably $10^2$ to $10^{10}$ cells/dose per adult human. The number of viable bacteria contained in a formulation is determined by an appropriate method depending on the type of bacteria, but can be easily determined by, for example, the plate culture method using tryptic soy agar plates with 5% defibrinated sheep blood as described later. The dosage of the agent when administered via a parenteral route may depend on the subject of administration (for example, an adult human), the intervals of administration (for example, one dose a day), etc., but the parenteral dose of the agent calculated based on the dry mass of the bacteria of the present invention may be, for example, about 0.0001 mg to about 100 g, about 0.001 mg to about 50 g, about 0.01 mg to about 20 g, about 0.1 mg to about 5 g, or the like, or the parenteral dose of the agent calculated based on the dry mass of a processed product of the bacteria of the present invention may be, for example, about 0.0001 mg to about 100 g, about 0.001 mg to about 50 g, about 0.01 mg to about 20 g, about 0.1 mg to about 5 g, or the like.

The intervals of administration are also selected as appropriate depending on the dosage form, the subject of administration, etc., and the agent may be administered, for example, about 1 to 3 times a day, or about 1 to 3 times every several months.

The frequency of administration is also selected as appropriate depending on the dosage form, the subject of administration, etc., and the agent may be administered in a single dose or continuously administered at certain intervals.

The agent of the present invention can be used to prepare various types of formulations (compositions, pharmaceutical compositions, food compositions, or cosmetic compositions) according to various embodiments. The present invention therefore includes such a composition containing the agent.

Medicament (Pharmaceutical Composition)

The present invention can be used to prepare a medicament comprising the agent of the present invention.

The medicament of the present invention may be produced by any method using the agent of the present invention as an ingredient, and may be produced by a conventionally known method or a method known per se.

The mode of administration (or the dosage form) of the medicament of the present invention may be any mode of administration (or any dosage form) that allows the medicament to prevent or treat small intestinal injury induced by an NSAID with a half-life of less than 14 hours and a PPI. The medicament may be administered, for example, via an oral route (as an oral medicament) or a parenteral route (as a parenteral medicament), etc.

The oral medicament may be prepared by, for example, combining the agent of the present invention with a pharmaceutically acceptable carrier. Examples of the oral medicament include, for example, solid dosage forms, such as tablets (for example, sugar-coated tablets etc.), pills, capsules, powders, coated tablets, granules, and troches; liquid dosage forms, such as solutions, suspensions, emulsions, syrups and elixirs; semi-solid dosage forms, such as jelly formulations; etc. Examples of the parenteral medicament include, for example, injections (for example, subcutaneous, intravenous, intramuscular, and intraperitoneal injections, intravenous drips, etc.), suppositories (for example, rectal suppositories, vaginal suppositories, etc.), topical medicaments (for example, transdermal formulations, ointments, transnasal formulations, etc.), etc.

The dosage form of the medicament of the present invention is not limited to a particular one, and may be, for example, a liquid, a fluid, a gel, a semi-solid, a solid, etc. The dosage form also includes liquid, fluid, gel, semi-solid, solid and other dosage forms that are prepared at the time of use.

The amount of the bacteria or a processed product thereof contained in the medicament of the present invention is not limited to a particular one, but the amount calculated based on the dry mass of the bacteria may be, for example, about 0.0001% by mass to about 50% by mass, about 0.001% by mass to about 30% by mass, about 0.01% by mass to about 10% by mass, or the like relative to the total mass of the medicament, and the amount calculated based on the dry mass of a processed product of the bacteria may be, for example, about 0.0001% by mass to about 50% by mass, about 0.001% by mass to about 30% by mass, about 0.01% by mass to about 10% by mass, or the like relative to the total mass of the medicament.

The dosage of the medicament of the present invention may be selected as appropriate depending on the dosage form, the route of administration, the subject of administration, the age and body weight of the subject, the intervals of administration, etc. The dosage of the medicament when administered via an oral route may depend on the subject of administration (for example, an adult human), the intervals of administration (for example, one dose a day), etc., but the oral dose of the medicament calculated based on the dry mass of the bacteria of the present invention may be, for example, about 0.0001 mg to about 10 g, about 0.001 mg to about 5 g, about 0.01 mg to about 1 g, about 0.1 mg to about 500 mg, or the like, or the oral dose of the medicament calculated based on the dry mass of a processed product of the bacteria of the present invention may be, for example, about 0.0001 mg to about 10 g, about 0.001 mg to about 5 g, about 0.01 mg to about 1 g, about 0.1 mg to about 500 mg, or the like. The dosage of the medicament when administered via a parenteral route may depend on the subject of administration (for example, an adult human), the intervals of administration (for example, one dose a day), etc., but the parenteral dose of the medicament calculated based on the dry mass of the bacteria of the present invention may be, for example, about 0.0001 mg to about 10 g, about 0.001 mg to about 5 g, about 0.01 mg to about 1 g, about 0.1 mg to about 500 mg, or the like, or the parenteral dose of the medicament calculated based on the dry mass of a processed product of the bacteria of the present invention may be, for example, about 0.0001 mg to about 10 g, about 0.001 mg to about 5 g, about 0.01 mg to about 1 g, about 0.1 mg to about 500 mg, or the like.

The intervals of administration are also selected as appropriate depending on the dosage form, the subject of administration, etc., and the medicament may be administered, for example, about 1 to 3 times a day, or about 1 to 3 times every several months.

The frequency of administration is also selected as appropriate depending on the dosage form, the subject of administration, etc., and the medicament may be administered in a single dose or continuously administered at certain intervals.

The medicament of the present invention, in any dosage form, can contain, in addition to the agent of the present invention, a pharmaceutically acceptable base material or carrier (for example, an aqueous solvent, a solid carrier, a polyalcohol, a vegetable oil, an oil base, etc.), a pharmaceutically acceptable additive (for example, a surfactant, a flavor or a cooling agent, an antiseptic, a bactericide or an antibacterial agent, a pH adjusting agent, a tonicity agent, a chelating agent, a buffering agent, a stabilizer, an antioxidant, a thickening agent, etc.), a physiologically active ingredient other than the agent of the present invention (for example, a vitamin, an amino acid, a sugar, a high molecular weight compound, etc.), a pharmacologically active ingredient (for example, an antibacterial ingredient, a bactericide ingredient, etc.), etc.

Food Product (Food Composition)

The agent of the present invention can be used in the field of food products. That is, the agent of the present invention may be a food additive etc. Such a food additive can be used to prepare a food product. The present invention therefore also includes a food product (a food composition) containing the agent.

Examples of the food product include food and drink products, such as supplemental foods, balanced nutritional foods, health foods, foods with nutrient function claims, foods for specified health use, foods with function claims, and foods for patients. These food and drink products may be produced by any method that allows the food and drink products to exhibit their preventive or improving effect on small intestinal injury induced by an NSAID with a half-life of less than 14 hours and a PPI. Specific examples of suitable food products include supplements in the form of a powder, granules, a capsule, a tablet, etc. In addition to the food products in the form as described above, the food and drink products also include, for example, fermented foods (dairy products) such as yogurt and cheese; confectionaries such as chewing gums, hard candies, gummy candies, tablet candies, cookies, cakes, chocolate, ice cream, jelly, mousse, pudding, biscuits, corn flakes, chewable tablets, wafers, and rice crackers; drinks such as carbonated drinks, soft drinks, milk beverages, coffee drinks, black tea drinks, fruit juice drinks, nutritional drinks, alcoholic drinks, and mineral water; powdered drinks such as powdered juice and powdered soup; seasonings such as dressing and sauce; bread; noodles; steamed fish paste such as fish cake; rice seasonings; etc. Besides such forms for oral intake, the food products may be in the form for enteral intake (a liquid food, etc.).

The amount of the agent contained in the food product of the present invention can be selected as appropriate depending on the age, sex and health conditions of the subject and other conditions, and adjusted as appropriate for the dosage, the form of the food product, or the like. The food product of the present invention containing a large amount of the agent of the present invention can also be provided to allow the agent to more effectively exhibit its improving or preventive effect.

The food product of the present invention may be produced by any method using the agent of the present invention as an ingredient, and may be produced by a conventionally known method or a method known per se. In the process of production of the food product of the present invention, the agent of the present invention may be added or blended by a conventional method.

The amount of the agent contained in the food product of the present invention is not limited to a particular one, and can be adjusted as appropriate depending on the type of the food product, the ingredients of the food product, etc.

The amount of the agent of the present invention to be ingested in the form of the food product of the present invention is not limited to a particular one, and can be adjusted as appropriate depending on the subject who ingests the food product, the age and sex of the subject, the type of food product, the ingredients of the food product, etc.

Cosmetic Product (Cosmetic Composition)

The agent of the present invention can be used in the field of cosmetics. The agent of the present invention has an anti-inflammatory effect, and therefore a cosmetic product of the present invention comprising the agent of the present invention is capable of preventing or treating inflammation of the skin, etc.

The cosmetic product of the present invention may be any type of cosmetic product that comprises the agent of the present invention, and includes those classified into quasi-drugs, such as medicated cosmetics, according to the definitions in the Pharmaceutical Affairs Law.

The shape, form, application, manner of use, etc. of the cosmetic product of the present invention are not limited to particular ones, and may be selected as appropriate depending on the subject who uses the cosmetic product, the age and sex of the subject, etc.

The cosmetic product of the present invention may be produced by any method using the agent of the present invention as an ingredient, and may be produced by a conventionally known method or a method known per se. The cosmetic product of the present invention may contain, in addition to the agent of the present invention, a base material or a carrier that can commonly be used in a cosmetic product, and may also contain, as needed, an additive (for example, an antioxidant, a surfactant, a thickener, a preservative, a pH adjusting agent, an antiseptic, a colorant, a flavor, etc.) and/or another active ingredient (for example, a moisturizing ingredient, an anti-inflammatory ingredient, an anti-bacterial or bactericide ingredient, a vitamin, a cell-activating ingredient, a blood circulation-promoting ingredient, a keratin-softening ingredient, a skin-whitening ingredient, an astringent ingredient, etc.), to the extent that the effects of the present invention are exhibited.

The cosmetic product, the food product and the medicament of the present invention as described above can typically be packaged in a container, a bag, etc. in a conventional manner. The container, bag, etc. may be any container, bag, etc. that are usable as a container for a cosmetic product, a food product and a medicament, and may be selected as appropriate from those conventionally known or those known per se depending on the form, shape and dosage form of the agent, the cosmetic product, the food product and the medicament of the present invention.

The animal as a subject of the present invention may be a human or a non-human animal, and includes mammals, but is not limited thereto. Examples of mammals include primates such as humans, monkeys, orangutans, chimpanzees, and gorillas; experimental animals such as rabbits and rodents such as mice, rats, hamsters, and guinea pigs; domestic animals such as cow, horses, pigs, sheep, and goats; pets such as dogs and cats; and birds such as chickens, ducks and geese. The mammals are preferably primates (such as humans) or pets, more preferably humans, dogs or cats, and further preferably humans.

The present invention includes embodiments in which the configurations as described above are combined in various ways to allow the effects of the present invention to be exhibited, without departing the technical scope of the present invention.

EXAMPLES

The present invention will be described in more detail with reference to Examples, but is not limited thereto.

Various modifications are possible by a person having ordinary skill in the art, without departing from the technical idea of the present invention.

1. Test 1 (Comparison of Hematocrit Values)
(1) Preparation of GAM Broth and GAM Agar Plates An amount of 59 g of GAM broth (NISSUI PHARMACEUTICAL CO., LTD.) was dissolved in 1000 mL of distilled water, and heat-sterilized at 115° C. for 15 minutes to prepare GAM broth.

An amount of 74 g of GAM agar (NISSUI PHARMACEUTICAL CO., LTD.) was dissolved in 1000 mL of distilled water, heat-sterilized at 115° C. for 15 minutes, dispensed into plates at 20 mL per plate, and allowed to solidify to prepare GAM agar plates.

(2) Preparation of Centrifuged Bacterial Cells

Frozen stocks of the following bacterial strains were statically cultured in GAM broth at 37° C. for 24 hours: the *Bifidobacterium bifidum* G9-1 strain (*B. bifidum* G9-1) (Accession No. NITE BP-817), the *Bifidobacterium longum* reference strain JCM (registered trademark) $1217^T$ (*B. longum* JCM 1217) (purchased from Japan Collection of Microorganisms (JCM), RIKEN BioResource Research Center), and the *Bifidobacterium infantis* reference strain JCM 1222T (*B. infantis* JCM 1222) (purchased from JCM). Each of the bacterial liquid cultures was inoculated into fresh GAM broth at a ratio (by volume) of liquid culture to GAM broth of 1:100, and statically cultured at 37° C. for 24 hours. The bacterial liquid cultures were then centrifuged, washed twice with physiological saline, and centrifuged again to give centrifuged bacterial cells.

(3) Measurement of Number of Viable Bacteria

The centrifuged bacterial cells were suspended in 0.75 mL of physiological saline. The suspension was ten-fold serially diluted, and 0.05 mL of the diluted bacterial liquids was streaked on GAM agar plates and cultured at 37° C. for 48 hours. The colonies appeared on the plates were counted, and the number of viable bacteria was calculated based on the dilution factor.

(4) Preparation of NSAIDs

Loxoprofen sodium dihydrate (Lox; Loxonin, FUJIFILM Wako Pure Chemical Corporation) was dissolved in physiological saline at a concentration of 2 mg/mL. Also, 2-(4-isobutylphenyl)propionic acid (Ibu; ibuprofen, Tokyo Chemical Industry Co., Ltd.) and acetylsalicylic acid (Asp; aspirin, FUJIFILM Wako Pure Chemical Corporation) were separately dissolved in a 5% $NaHCO_3$ solution at a concentration of 2 mg/mL.

(5) Preparation of PPIs

Omepral (registered trademark) Injection 20 (ingredient: omeprazole (omz), AstraZeneca K.K.) and Takepron (registered trademark) INTRAVENOUS 30 mg (ingredient: lansoprazole (lpz), Takeda Pharmaceutical Company Limited.) were separately diluted in physiological saline at a concentration of 4 mg/mL. Takecab Tablets 20 mg (ingredient: vonoprazan (vpz) fumarate, Takeda Pharmaceutical Company Limited.) were crushed, then distilled water was added to a concentration of 4 mg/mL, and the mixture was warmed in a hot bath at 55° C. for 15 minutes to prepare a suspension.

(6) In Vivo Experiments

Six-week old Wister male rats (CHARLES RIVER LABORATORIES JAPAN, INC.) were kept under the conditions of room temperature of 22±5° C., humidity of 55±5% and a light cycle of 12 hours (7 a.m. to 7 p.m.). The animals were allowed to free access to a solid diet (CE-2, CLEA Japan, Inc.) and tap water.

The experimental schedule is shown in FIG. 1. At the start of the experiments, the blood was collected from the tail vein with hematocrit capillary tubes (Thermo Fisher Scientific K.K.) to measure hematocrit values. Based on the hematocrit values, the animals were divided into the following groups: a normal group (a group that received vehicle alone), NSAID alone administration groups (in FIGS. 2 to 9, Asp represents an aspirin alone administration group, Lox represents a Loxonin alone administration group, and Ibu represents an ibuprofen alone administration group), a control group (an NSAID and PPI administration group), and bifidobacteria administration groups (NSAID, PPI and bifidobacteria administration groups). After grouping, the body weight of the animals was measured for nine days, and one of the PPIs (10 mg/kg) was intraperitoneally administered twice a day. For the normal group and the NSAID alone administration groups, vehicle was administered instead of the PPIs. From day 6 of PPI administration, one of the NSAIDs (10 mg/kg) was administered by oral gavage twice a day. For the normal group, vehicle was administered instead of the NSAIDs. For the bifidobacteria administration groups, one strain of the bacteria ($1 \times 10^9$ cfu (colony forming unit)/animal) was further administered by oral gavage once a day. For the other groups, physiological saline was administered instead of the bifidobacteria. On the final day of the experiments, the hematocrit values were measured again, and the difference between the start and the end of the experiments was calculated and expressed as the rate of change of the hematocrit values. In aspirin administration experiments, the animals were fed with a high-fructose diet (EPS EKISHIN Co., Ltd) from the starting day of PPI administration.

2. Results and Discussion of Test 1
(a) Inhibitory Effects on Small Intestinal Injury Induced by Aspirin and Omeprazole As apparent from FIG. 2, administration of the *Bifidobacterium* bacteria inhibited hematocrit reduction induced by aspirin and omeprazole. The results confirmed that the *Bifidobacterium* bacteria inhibit small intestinal injury induced by aspirin and omeprazole. *Bifidobacterium bifidum* showed a higher inhibitory effect on small intestinal injury induced by aspirin and omeprazole.

Figure 3:
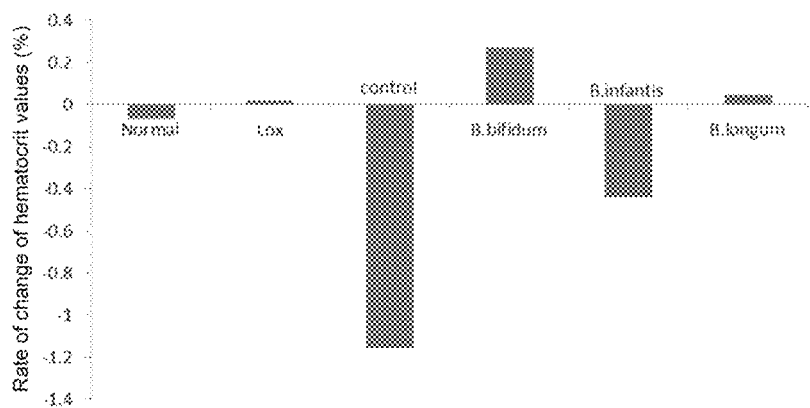
FIG. 3 shows the results of experiments for evaluating inhibitory effects on small intestinal injury induced by Loxonin and omeprazole, as assessed by determining the rate of change of hematocrit values (%). The data show the mean (n=5).

(b) Inhibitory Effects on Small Intestinal Injury Induced by Loxonin and Omeprazole As apparent from FIG. 3, administration of the *Bifidobacterium* bacteria inhibited hematocrit reduction induced by Loxonin and omeprazole. The results confirmed that the *Bifidobacterium* bacteria inhibit small intestinal injury induced by Loxonin and omeprazole. *Bifidobacterium bifidum* showed a higher inhibitory effect on small intestinal injury induced by Loxonin and omeprazole.

Figure 4:
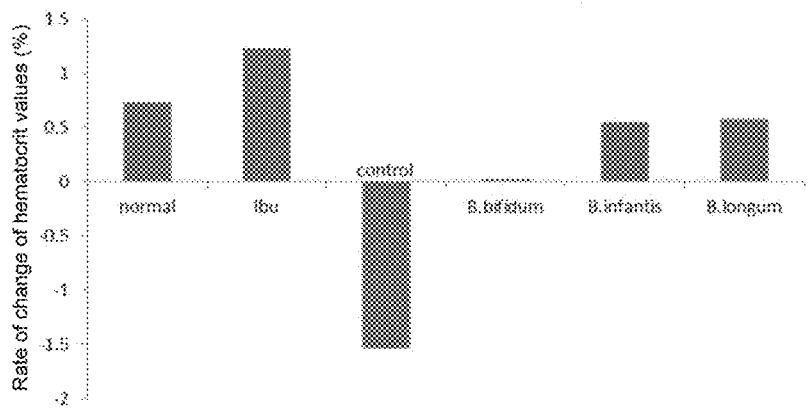
FIG. 4 shows the results of experiments for evaluating inhibitory effects on small intestinal injury induced by ibuprofen and omeprazole, as assessed by determining the rate of change of hematocrit values (%). The data show the mean (n=5).

(c) Inhibitory Effects on Small Intestinal Injury Induced by Ibuprofen and Omeprazole As apparent from FIG. 4, administration of the *Bifidobacterium* bacteria inhibited hematocrit reduction induced by ibuprofen and omeprazole. The results confirmed that the *Bifidobacterium* bacteria inhibit small intestinal injury induced by ibuprofen and omeprazole. *Bifidobacterium infantis* and *Bifidobacterium longum* showed a higher inhibitory effect on small intestinal injury induced by ibuprofen and omeprazole.

Figure 5:
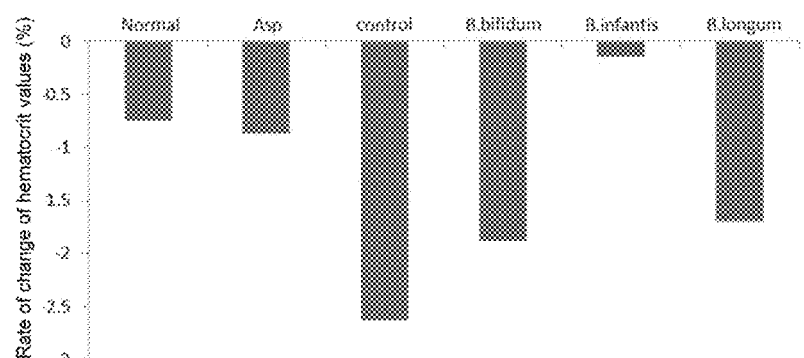
FIG. 5 shows the results of experiments for evaluating inhibitory effects on small intestinal injury induced by aspirin and lansoprazole, as assessed by determining the rate of change of hematocrit values (%). The data show the mean (n=5).

(d) Inhibitory Effects on Small Intestinal Injury Induced by Aspirin and Lansoprazole As apparent from FIG. 5, administration of the *Bifidobacterium* bacteria inhibited hematocrit reduction induced by aspirin and lansoprazole. The results confirmed that the *Bifidobacterium* bacteria inhibit small intestinal injury induced by aspirin and lansoprazole. *Bifidobacterium infantis* showed a higher inhibitory effect on small intestinal injury induced by aspirin and lansoprazole.

Figure 6:
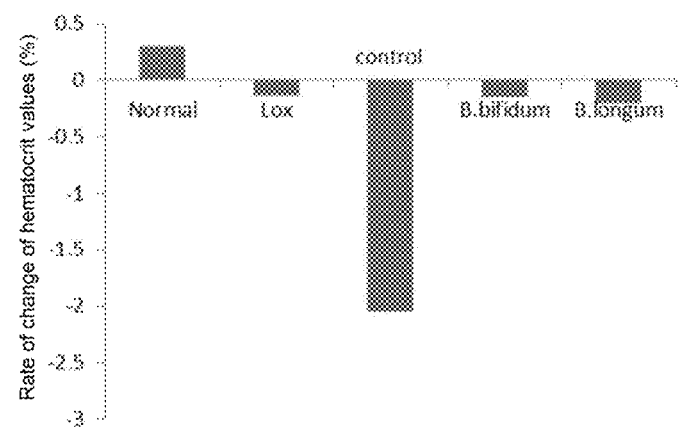
FIG. 6 shows the results of experiments for evaluating inhibitory effects on small intestinal injury induced by Loxonin and lansoprazole, as assessed by determining the rate of change of hematocrit values (%). The data show the mean (n=5).

(e) Inhibitory Effects on Small Intestinal Injury Induced by Loxonin and Lansoprazole As apparent from FIG. 6, administration of the *Bifidobacterium* bacteria inhibited hematocrit reduction induced by Loxonin and lansoprazole. The results confirmed that the *Bifidobacterium* bacteria inhibit small intestinal injury induced by Loxonin and lansoprazole.

Figure 7:
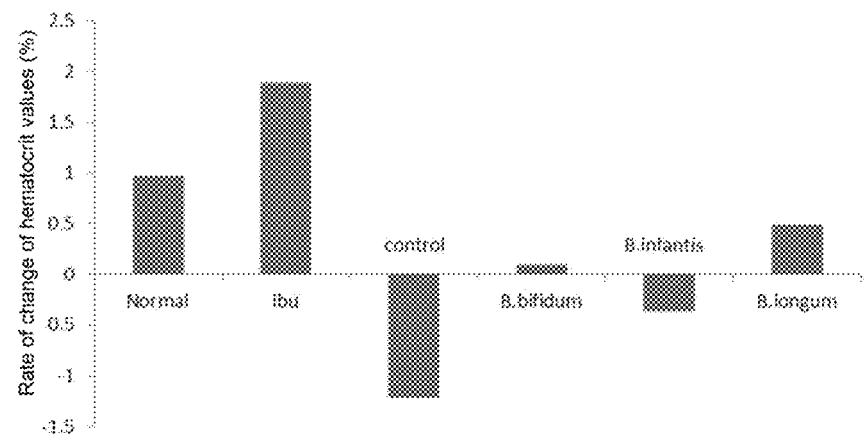
FIG. 7 shows the results of experiments for evaluating inhibitory effects on small intestinal injury induced by ibuprofen and lansoprazole, as assessed by determining the rate of change of hematocrit values (%). The data show the mean (n=5).

(f) Inhibitory Effects on Small Intestinal Injury Induced by Ibuprofen and Lansoprazole As apparent from FIG. 7, administration of the *Bifidobacterium* bacteria inhibited hematocrit reduction induced by ibuprofen and lansoprazole. The results confirmed that the *Bifidobacterium* bacteria inhibit small intestinal injury induced by ibuprofen and lansoprazole. *Bifidobacterium longum* showed a higher inhibitory effect on small intestinal injury induced by ibuprofen and lansoprazole.

Figure 8:
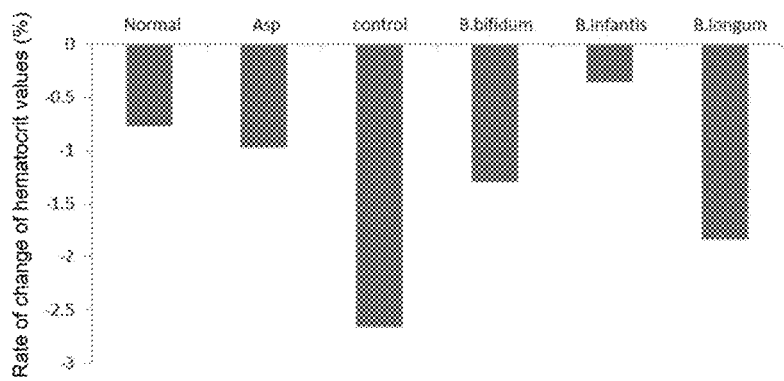
FIG. 8 shows the results of experiments for evaluating inhibitory effects on small intestinal injury induced by aspirin and vonoprazan fumarate, as assessed by determining the rate of change of hematocrit values (%). The data show the mean (n=5).

(g) Inhibitory Effects on Small Intestinal Injury Induced by Aspirin and Vonoprazan Fumarate As apparent from FIG. 8, administration of the *Bifidobacterium* bacteria inhibited hematocrit reduction induced by aspirin and vonoprazan fumarate. The results confirmed that the *Bifidobacterium* bacteria inhibit small intestinal injury induced by aspirin and vonoprazan fumarate. *Bifidobacterium infantis* showed a higher inhibitory effect on small intestinal injury induced by aspirin and vonoprazan fumarate.

Figure 9:
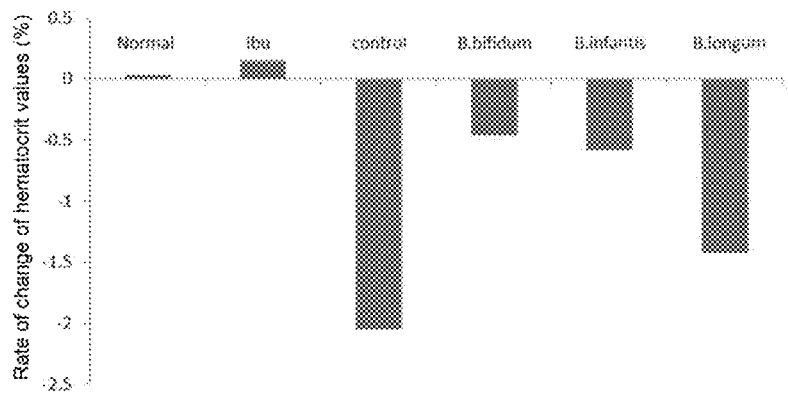
FIG. 9 shows the results of experiments for evaluating inhibitory effects on small intestinal injury induced by ibuprofen and vonoprazan fumarate, as assessed by determining the rate of change of hematocrit values (%). The data show the mean (n=5).

(h) Inhibitory Effects on Small Intestinal Injury Induced by Ibuprofen and Vonoprazan Fumarate As apparent from FIG. 9, administration of the *Bifidobacterium* bacteria inhibited hematocrit reduction induced by ibuprofen and vonoprazan fumarate. The results confirmed that the *Bifidobacterium* bacteria inhibit small intestinal injury induced by ibuprofen and vonoprazan fumarate. *Bifidobacterium bifidum* and *Bifidobacterium infantis* showed a higher inhibitory effect on small intestinal injury induced by ibuprofen and vonoprazan fumarate.

(i) Comparative Example 1

Bifidobacteria administration was not performed. Omeprazole was used as a PPI, and sulindac (FUJIFILM Wako Pure Chemical Corporation, dissolved in a 5% $NaHCO_3$ solution) was used as an NSAID.

Figure 10:
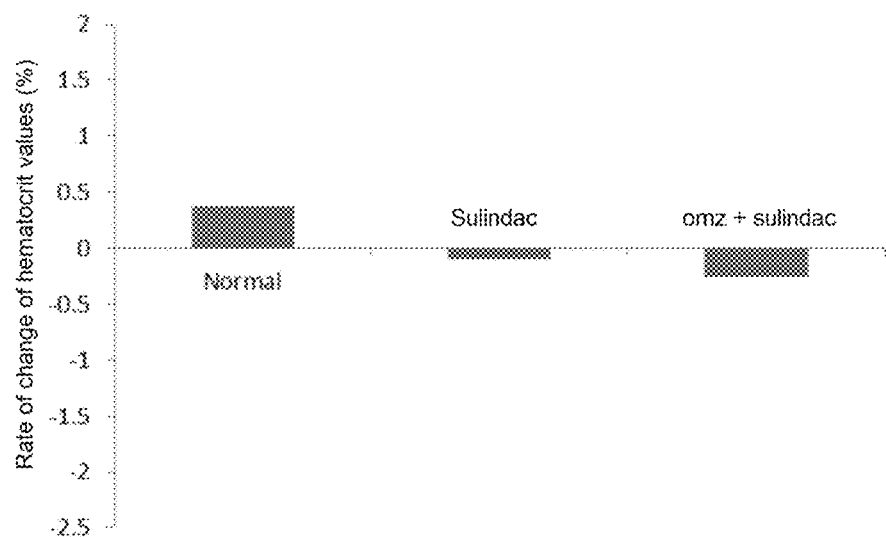
FIG. 10 shows the results of the experiments for evaluating the degree of small intestinal injury induction when sulindac was used as an NSAID and omeprazole was used as a PPI, as assessed by determining the rate of change of hematocrit values (%). The data show the mean (n=5).

In FIG. 10, Sulindac represents a sulindac alone administration group, and omz+sulindac represents an omeprazole and sulindac administration group. As shown in FIG. 10, sulindac in combination with omeprazole did not induce reduction of the hematocrit values, indicating that small intestinal injury is induced by a combination of a particular NSAID and a PPI.

(j) Comparative Example 2

Small intestinal injury was induced by a combination of (S)-(+)-2-(6-methoxy-2-naphthyl)propionic acid (naproxen, Tokyo Chemical Industry Co., Ltd., dissolved in a 5% $NaHCO_3$ solution; also called NAP) and omeprazole (omz) or by a combination of ibuprofen (Ibu) and omeprazole (omz). The recovery rates were compared between the combinations to determine whether any stronger effect could be observed. That is, the effect of *B. bifidum* on recovery from small intestinal injury induced by ibuprofen and omeprazole when compared with the effect of *B. bifidum* on recovery from small intestinal injury induced by naproxen and omeprazole was calculated by the following formula, taking the latter effect as 1.

$$\text{Recovery rate} = \frac{(\text{Hematocrit value of } omz + Ibu + B.\ bifidum) - (\text{Hematocrit value of } omz + Ibu)}{(\text{Hematocrit value of } omz + NAP + B.\ bifidum) - (\text{Hematocrit value of } omz + NAP)}$$

Figure 11:
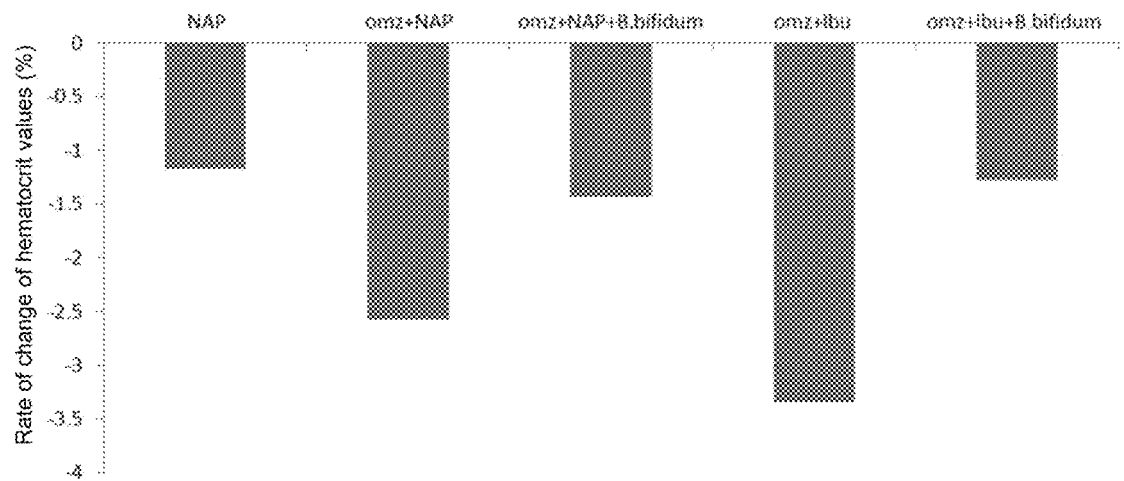
FIG. 11 shows the results of experiments for evaluating inhibitory effects on small intestinal injury induced by naproxen and omeprazole and on small intestinal injury induced by ibuprofen and omeprazole, as assessed by determining the rate of change of hematocrit values (%). The data show the mean (n=8).

As apparent from FIG. 11, *B. bifidum* G9-1 showed an inhibitory effect on small intestinal injury induced by naproxen and omeprazole. *B. bifidum* G9-1 also showed an inhibitory effect on small intestinal injury induced by ibuprofen and omeprazole.

Figure 12:
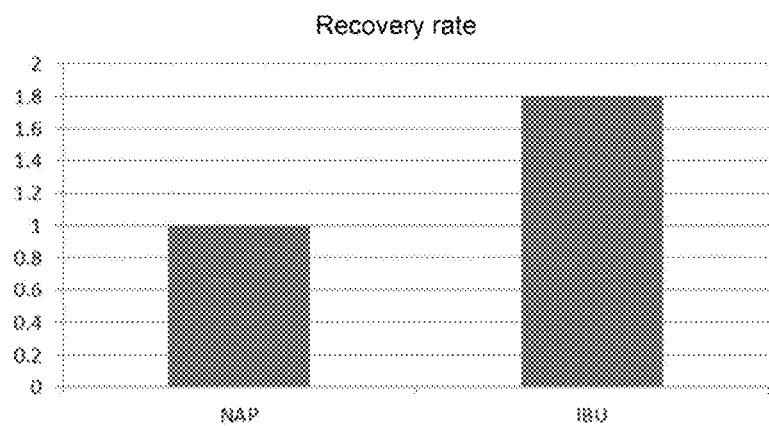
FIG. 12 shows the results of experiments for evaluating inhibitory effects on small intestinal injury induced by naproxen and omeprazole and on small intestinal injury induced by ibuprofen and omeprazole, as assessed by determining the recovery rate (n=1).

Also as apparent from FIG. 12, the recovery rate was 1.8-fold higher when ibuprofen was used as an NSAID than when naproxen was used as an NSAID.

The above results demonstrated a higher recovery rate as compared with the recovery rate from small intestinal injury induced by naproxen and omeprazole as described in Non-Patent Literature 1, indicating the unexpected, advantageous effects of the present invention over Non-Patent Literature 1.

3. Test 2 (Comparison of Intestinal Permeabilities and of the Numbers of Villi in the Jejunum)

(1) Preparation of Bacterial Cells

GAM broth and GAM agar plates were prepared in the same manner as in Test Example 1.

The *Bifidobacterium bifidum* G9-1 strain (*B. bifidum* G9-1) (Accession No. NITE BP-817) was used as bacterial cells. Centrifuged bacterial cells were prepared and the number of viable bacteria was measured in the same manner as in Test Example 1.

A bacterial liquid equivalent to $1 \times 10^9$ CFU was heated at 90° C. for 15 minutes to prepare dead bacterial cells.

(2) Preparation of NSAID

Acetylsalicylic acid (Asp; aspirin, FUJIFILM Wako Pure Chemical Corporation) was dissolved in a 5% $NaHCO_3$ solution at a concentration of 20 mg/mL.

(3) Preparation of PPI

Omepral (registered trademark) Injection 20 (ingredient: omeprazole, AstraZeneca K.K.) was diluted in physiological saline at a concentration of 2 mg/mL.

(4) In Vivo Experiments

Five-week old C57BL/6JJc1 male mice (CLEA Japan, Inc.) were purchased and kept under the conditions of room temperature of 22±5° C., humidity of 55±5% and a light cycle of 12 hours (7 a.m. to 7 p.m.). The animals were allowed to free access to a CE-2 diet (CLEA Japan, Inc.) during acclimation and to a high-fructose diet (EPS EKISHIN Co., Ltd) during the experiments.

Experimental groups included a vehicle group (a vehicle alone administration group), an Asp group (an aspirin alone administration group), a PPI group (a PPI alone administration group), a control group (an aspirin+PPI combined administration group), a G9-1 group (an aspirin+PPI+G9-1 viable bacteria group), a heat-killed G9-1 group (an aspirin+PPI+G9-1 dead bacteria group), and an acetate group (an aspirin+PPI+acetic acid administration group). After one-week acclimation, the animals were divided into the above groups based on the body weight.

Figure 13:
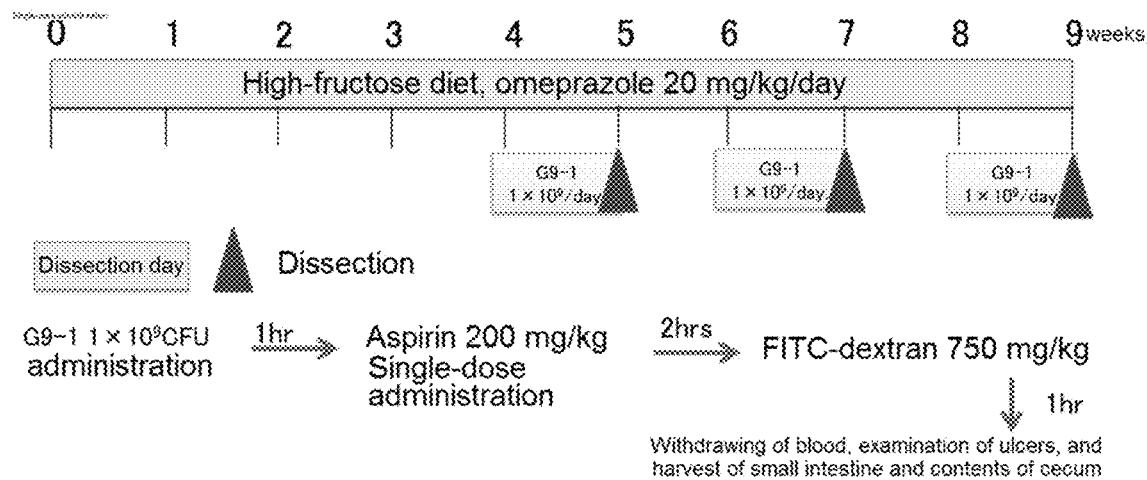
FIG. 13 shows the experimental schedule for Test 2.

FIG. 13 shows the experimental schedule. Omeprazole 20 mg/kg (AstraZeneca) was intraperitoneally administered once a day (vehicle was intraperitoneally administered for the vehicle group and the Asp group). This administration was continued until the end of experiments (for 9 weeks). From one week prior to dissection, G9-1 ($1\times10^9$ CFU) was orally administered after omeprazole administration. For the dead bacteria administration group, heat-killed bacteria at the same CFU were administered. For the acetic acid administration group, the animals were allowed to free access to 0.15 M acetic acid prepared by diluting acetic acid (FUJIFILM Wako Pure Chemical Corporation) in sterilized water at a concentration of 0.15 M. For the vehicle group, the Asp group and the control group, vehicle was orally administered. On the final day of the experiments, acetylsalicylic acid (FUJIFILM Wako Pure Chemical Corporation) was orally administered at 200 mg/kg one hour after G9-1 administration (for the vehicle group, vehicle was orally administered). Two hours later, FITC-dextran (Sigma) was orally administered at 750 mg/kg. One hour later, the plasma was collected, and the fluorescence intensity of FITC was measured with a plate reader (Tecan).

The animals were dissected and the jejunum was harvested. After washing off the contents of the jejunum, the specimens were fixed in 10% neutral buffered formalin solution (FUJIFILM Wako Pure Chemical Corporation), and stained by HE staining at Biopathology Institute Co., Ltd. The stained specimens were observed under a microscope to determine the number of the villi.

4. Results and Discussion of Test 2

Figure 14A:
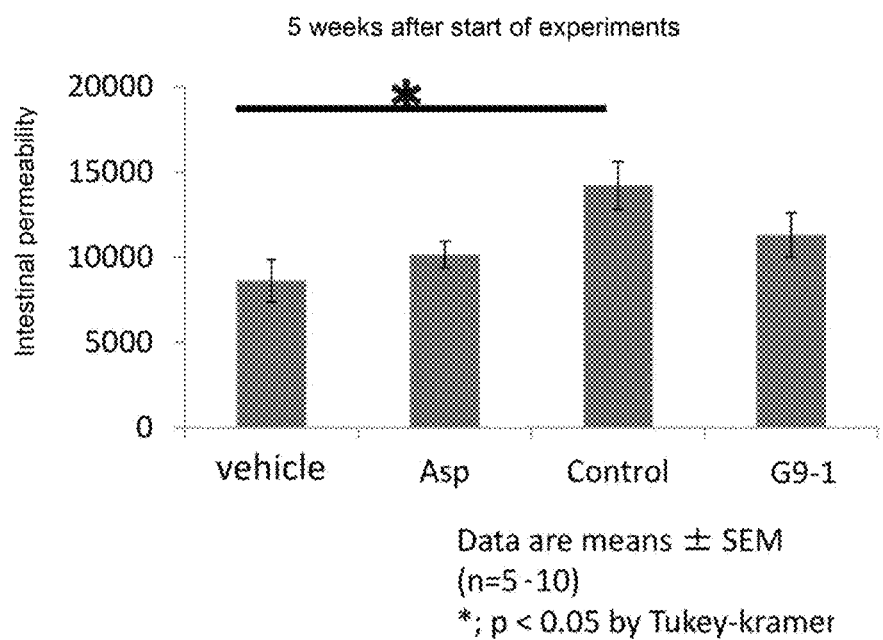
FIG. 14A shows the results of experiments for evaluating inhibitory effects on small intestinal injury induced by aspirin and omeprazole, as assessed by determining intestinal permeability five weeks after the start of the experiments. The vertical axis in FIG. 14A shows the fluorescence intensity in the plasma (unit: arbitrary unit (AU)). The data show the mean±SEM (n=5 to 10). *; p<0.05, by Tukey-Kramer.
Figure 14B:
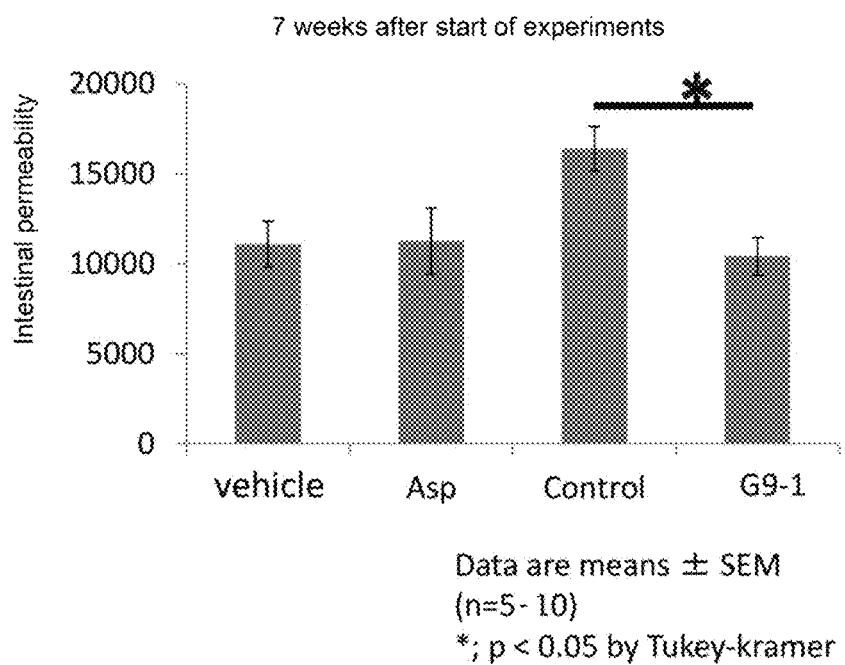
FIG. 14B shows the results of experiments for evaluating inhibitory effects on small intestinal injury induced by aspirin and omeprazole, as assessed by determining intestinal permeability seven weeks after the start of the experiments. The vertical axis in FIG. 14B shows the fluorescence intensity in the plasma (unit: arbitrary unit (AU)). The data show the mean±SEM (n=5 to 10). *; p<0.05, by Tukey-Kramer.
Figure 14C:
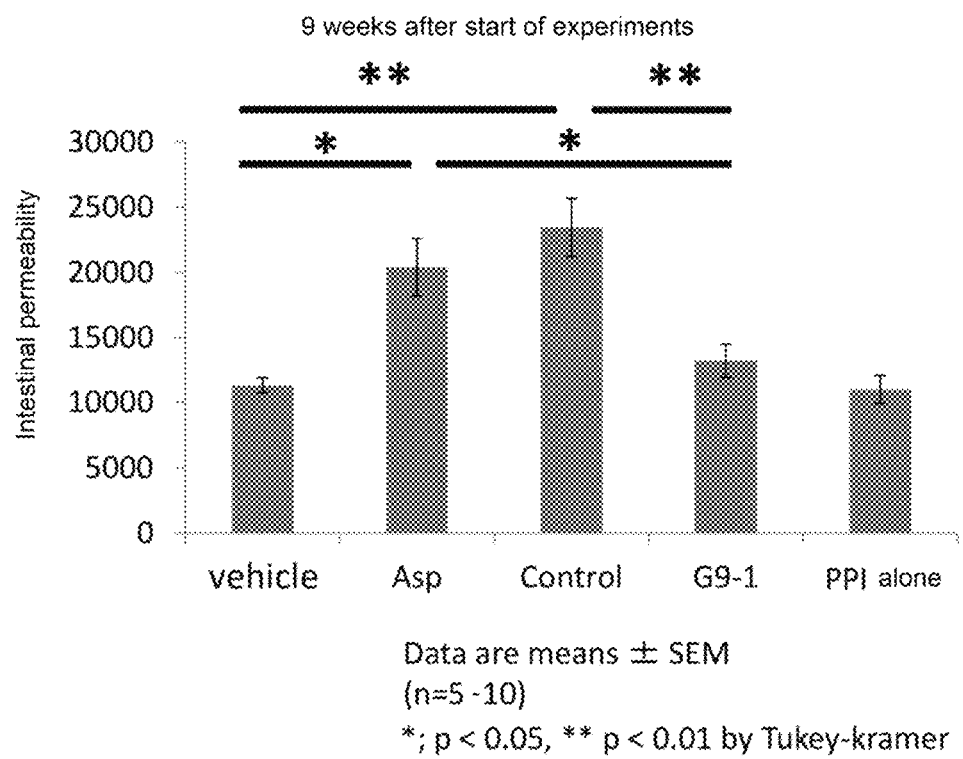
FIG. 14C shows the results of experiments for evaluating inhibitory effects on small intestinal injury induced by aspirin and omeprazole, as assessed by determining intestinal permeability nine weeks after the start of the experiments. The vertical axis in FIG. 14C shows the fluorescence intensity in the plasma (unit: arbitrary unit (AU)). The data show the mean±SEM (n=5 to 10). *; p<0.05, by Tukey-Kramer. **; p<0.01, by Tukey-Kramer.

(a) Inhibitory Effects on Enhanced Intestinal Permeability Induced by Aspirin and Omeprazole The experimental results of the intestinal permeability 5, 7 and 9 weeks after the start of the experiments are shown in FIGS. 14A, 14B and 14C, respectively.

As apparent from FIGS. 14A, 14B and 14C, administration of the *Bifidobacterium* bacteria inhibited increased fluorescence intensity in the plasma induced by aspirin alone or a combination of aspirin and omeprazole. Higher fluorescence intensity in the plasma indicates greater leakage of the fluorescent dye into the blood, i.e., more enhanced intestinal permeability and occurrence of more severe small intestinal injury. The results confirmed that the *Bifidobacterium* bacteria inhibit small intestinal injury induced by aspirin and omeprazole.

Figure 15A:
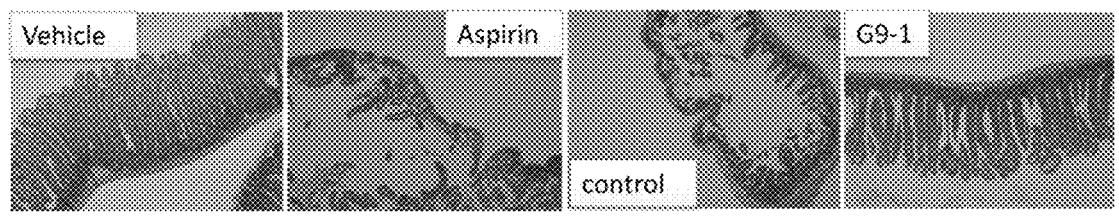
FIG. 15A shows the results of experiments for evaluating inhibitory effects on small intestinal injury induced by aspirin and omeprazole, as assessed by observing micrographs of the villi stained by HE staining nine weeks after the start of the experiments.
Figure 15B:
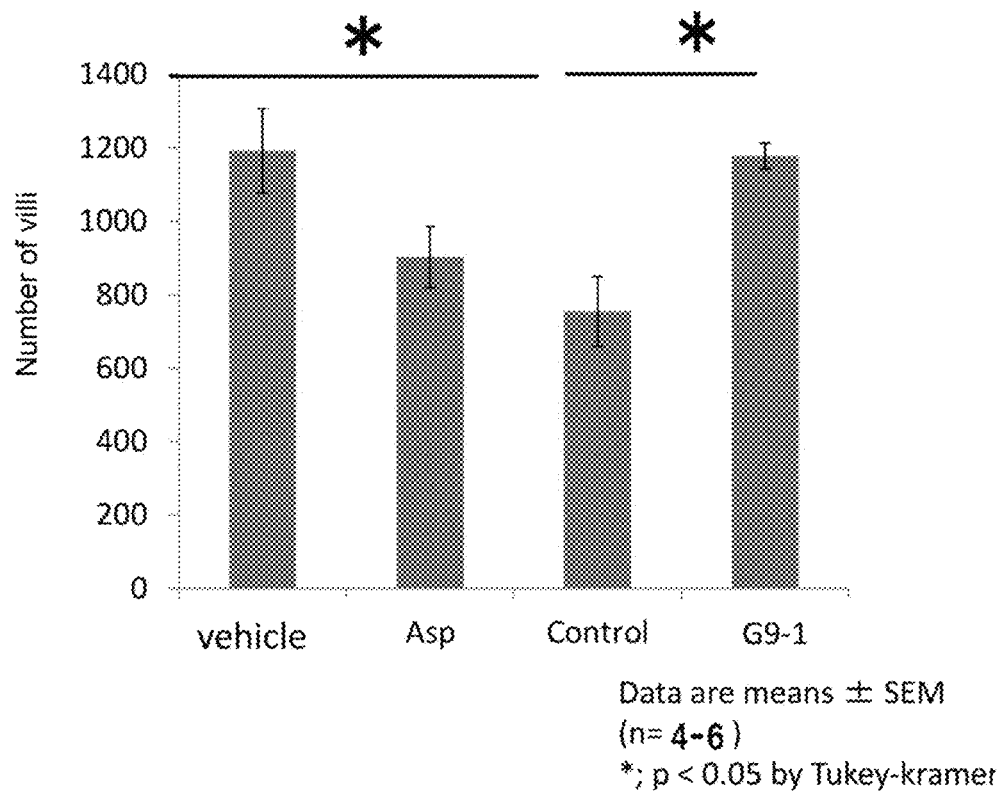
FIG. 15B shows the results of experiments for evaluating inhibitory effects on small intestinal injury induced by aspirin and omeprazole, as assessed by determining the number of the villi nine weeks after the start of the experiments. The data show the mean±SEM (n=4 to 6). *; p<0.05, by Tukey-Kramer.

(b) Inhibitory Effects on Decrease in the Number of Villi in the Jejunum Induced by Aspirin and Omeprazole The experimental results of the number of villi in the jejunum 9 weeks after the start of the experiments are shown in FIGS. 15A and 15B.

As apparent from FIGS. 15A and 15B, administration of the *Bifidobacterium* bacteria inhibited decrease in the number of villi in the jejunum induced by aspirin alone or a combination of aspirin and omeprazole. Greater decrease in the number of villi in the jejunum indicates occurrence of more severe small intestinal injury. The results confirmed that the *Bifidobacterium* bacteria inhibit small intestinal injury induced by aspirin and omeprazole.

Figure 16:
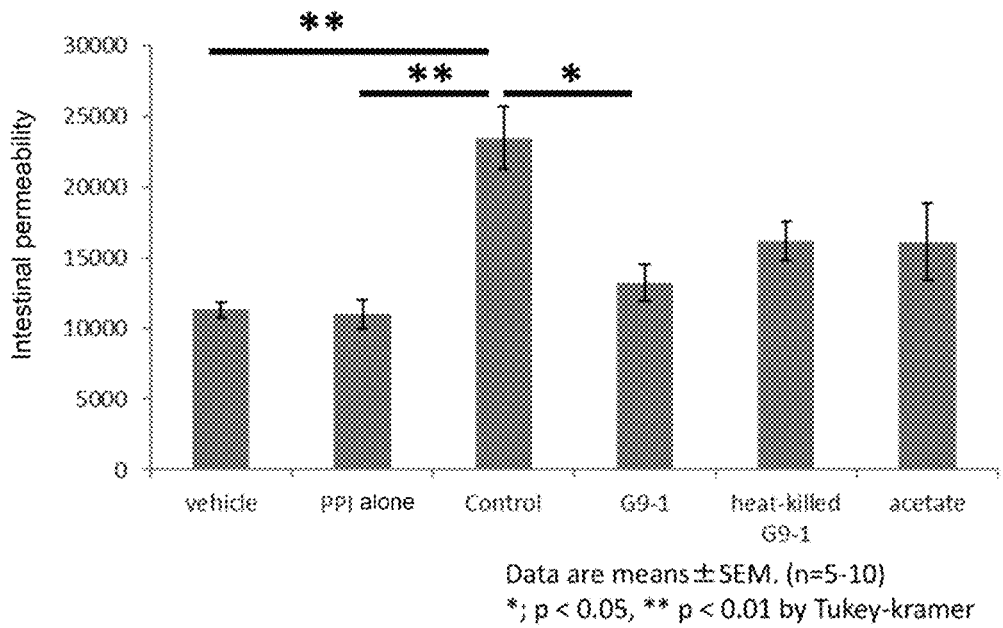
FIG. 16 shows the results of experiments for evaluating inhibitory effects on small intestinal injury induced by aspirin and omeprazole, as assessed by determining intestinal permeability nine weeks after the start of the experiments. The vertical axis in FIG. 16 shows the fluorescence intensity in the plasma (unit: arbitrary unit (AU)). The data show the mean±SEM (n=5 to 10). *; p<0.05, by Tukey-Kramer. **; p<0.01, by Tukey-Kramer.

(c) Inhibitory Effects of Dead Bacteria or Metabolites of Viable Bacteria on Enhanced Intestinal Permeability Induced by Aspirin and Omeprazole The experimental results of the intestinal permeability 9 weeks after the start of the experiments are shown in FIG. 16.

As apparent from FIG. 16, administration of the dead *Bifidobacterium* bacteria or acetic acid, which is one of metabolites of viable *Bifidobacterium* bacteria, inhibited increased fluorescence intensity in the plasma induced by aspirin alone or a combination of aspirin and omeprazole. Higher fluorescence intensity in the plasma indicates greater leakage of the fluorescent dye into the blood, i.e., more enhanced intestinal permeability and occurrence of more severe small intestinal injury. The results confirmed that the dead *Bifidobacterium* bacteria or acetic acid, which is one of metabolites of viable *Bifidobacterium* bacteria, inhibits small intestinal injury induced by aspirin and omeprazole.

INDUSTRIAL APPLICABILITY

An agent of the present invention for preventing or treating small intestinal injury induced by an NSAID with a half-life of less than 14 hours and a PPI alleviates the adverse side effects of the NSAID and the PPI, and is therefore useful in the pharmaceutical field.

The invention claimed is:

1. A method for preventing or treating:
   (i) small intestinal injury induced by a non-steroidal anti inflammatory drug with a half-life of less than 14 hours and a proton pump inhibitor, or
   (ii) a fat-associated disease and/or inflammation accompanying small intestinal injury induced by a non-steroidal anti-inflammatory drug with a half-life of less than 14 hours and a proton pump inhibitor,
   the method comprising the step of administering a *Bifidobacterium bifidum* G9-1 or a processed product thereof to a human or a non-human animal in need thereof, wherein the processed product thereof is one or more selected from a disrupted bacterial cell suspension, culture medium or culture supernatant of the bacterial cells, solid residues separated from such disrupted cell suspension, culture medium or culture supernatant by a solid-liquid separation technique, dead cells of the bacteria, and acetic acid,
   a dosage of the bacteria is 0.0001 mg to 100 g which calculated based on the dry mass of the bacteria or the processed product of the bacteria, and
   the administration of the bacteria is started on the same day as administration of the non-steroidal anti-inflammatory drug.

2. The method according to claim 1, wherein the non-steroidal anti-inflammatory drug with a half-life of less than 14 hours is one or more selected from the group consisting of aspirin, loxoprofen, ibuprofen, diclofenac, celecoxib, etodolac, pranoprofen, flurbiprofen axetil, lornoxicam, tiaramide, zaltoprofen, and pharmaceutically acceptable salts thereof.

3. The method according to claim 1, wherein the proton pump inhibitor is one or more selected from the group consisting of omeprazole, lansoprazole, rabeprazole, esomeprazole, vonoprazan, tegoprazan, (R)-2-[4(2,2-dimethyl-1,3-dioxan-5-yl)methoxy-3,5-dimethylpyridin-2-yl]methylsulfinyl-1H-benzimidazole, and pharmaceutically acceptable salts thereof.

4. The method according to claim 1, wherein the processed product of the *Bifidobacterium bifidum* G9-1 contains acetic acid.

5. The method according to claim 1, wherein the *Bifidobacterium bifidum* G9-1 or a processed product thereof is contained in a pharmaceutical composition, a food composition, or a cosmetic composition.

\* \* \* \* \*